US011707572B2

(12) United States Patent
Murakami et al.

(10) Patent No.: US 11,707,572 B2
(45) Date of Patent: Jul. 25, 2023

(54) DRUG INJECTION DEVICE

(71) Applicant: PHC HOLDINGS CORPORATION, Tokyo (JP)

(72) Inventors: Kenji Murakami, Ehime (JP); Mitsuteru Fujimoto, Ehime (JP); Seiji Kikuchi, Ehime (JP); Toru Aoki, Ehime (JP); Masakazu Mori, Ehime (JP); Ryosuke Tani, Ehime (JP); Shinichi Kojima, Ehime (JP); Yoshihiro Kataoka, Ehime (JP); Katsumi Nakanishi, Ehime (JP); Tsuguhiro Kondo, Ehime (JP); Takashi Morimoto, Ehime (JP); Akio Inoki, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 419 days.

(21) Appl. No.: 17/109,575

(22) Filed: Dec. 2, 2020

(65) Prior Publication Data

US 2021/0085875 A1 Mar. 25, 2021

Related U.S. Application Data

(62) Division of application No. 15/779,005, filed as application No. PCT/JP2016/087101 on Dec. 13, 2016, now Pat. No. 10,881,801.

(30) Foreign Application Priority Data

Dec. 24, 2015 (JP) .............................. JP2015-252431

(51) Int. Cl.
*A61M 5/24* (2006.01)
*A61M 5/145* (2006.01)
*A61M 5/20* (2006.01)

(52) U.S. Cl.
CPC ............ *A61M 5/24* (2013.01); *A61M 5/1456* (2013.01); *A61M 5/1458* (2013.01);
(Continued)

(58) Field of Classification Search
CPC .. A61M 2005/2403; A61M 2005/2407; A61M 2005/2411; A61M 2005/2414; A61M 2005/2485; A61M 2005/2492
See application file for complete search history.

(56) References Cited

U.S. PATENT DOCUMENTS

| 5,647,851 A | * | 7/1997 | Pokras ................... A61M 5/20 604/131 |
| 2005/0171476 A1 | | 8/2005 | Judson et al. |

(Continued)

FOREIGN PATENT DOCUMENTS

| JP | H11-128345 A | 5/1999 |
| JP | 2012-050847 A | 3/2012 |

(Continued)

OTHER PUBLICATIONS

International Search Report issued in International Application No. PCT/JP2016/087101 dated Mar. 7, 2017 (with English translation).

(Continued)

*Primary Examiner* — William R Carpenter
(74) *Attorney, Agent, or Firm* — McDermott Will & Emery LLP

(57) ABSTRACT

A cartridge adapter includes: a cartridge holder having a space that can accommodate therein a drug cartridge, the drug cartridge including a cylinder having a tubular internal space extending in a longitudinal direction, a gasket supported in the internal space so as to be movable in the longitudinal direction, and a drug held in the internal space; a piston that moves the gasket in the longitudinal direction in the internal space of the cylinder; a piston guide that (Continued)

movably supports the piston and connected to the cartridge holder; and a piston driving mechanism that drives the piston in the longitudinal direction.

12 Claims, 29 Drawing Sheets

(52) U.S. Cl.
CPC . *A61M 5/14546* (2013.01); *A61M 2005/2013* (2013.01); *A61M 2205/50* (2013.01)

(56) References Cited

U.S. PATENT DOCUMENTS

| | | | |
|---|---|---|---|
| 2007/0197968 | A1 | 8/2007 | Pongpairochana et al. |
| 2008/0319383 | A1 | 12/2008 | Byland et al. |
| 2012/0279329 | A1 | 11/2012 | Veasey et al. |
| 2013/0218128 | A1* | 8/2013 | Cowe ............... A61M 5/3204 604/506 |
| 2014/0012229 | A1 | 1/2014 | Bokelman et al. |
| 2014/0330206 | A1* | 11/2014 | Moore ............. A61M 5/14216 604/152 |
| 2015/0045729 | A1 | 2/2015 | Denzer et al. |
| 2015/0328404 | A1 | 11/2015 | Murakami et al. |
| 2017/0258999 | A1 | 9/2017 | Hoeholt et al. |

FOREIGN PATENT DOCUMENTS

| | | |
|---|---|---|
| JP | 2013-506467 A | 2/2013 |
| JP | 2014-516634 A | 7/2014 |
| JP | 2015-521920 A | 8/2015 |
| WO | 2011/129175 A1 | 10/2011 |

OTHER PUBLICATIONS

Non-Final Office Action issued in U.S. Appl. No. 15/779,005, dated Apr. 7, 2020.

Notice of Allowance issued in U.S. Appl. No. 15/779,005, dated Sep. 23, 2020.

* cited by examiner

FIG.2
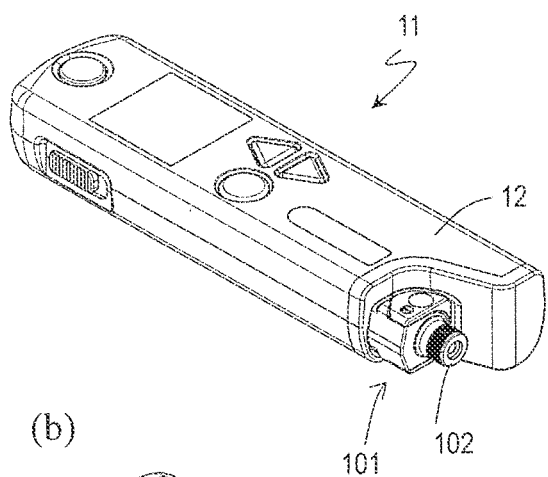
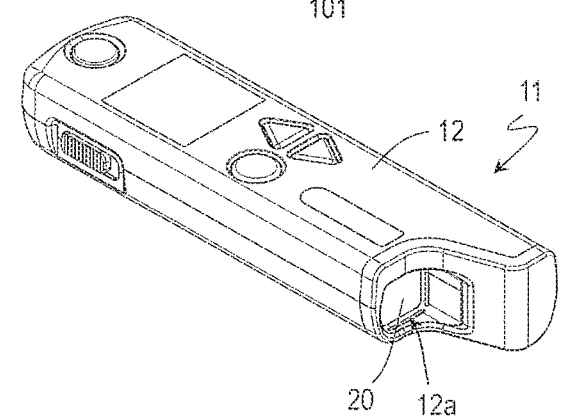
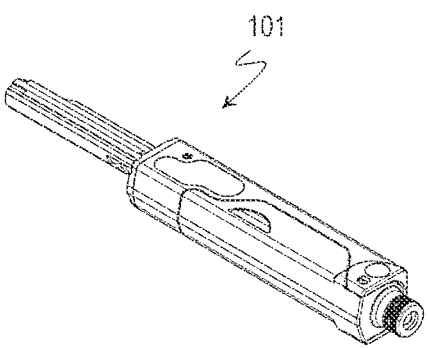

FIG.8
(a)
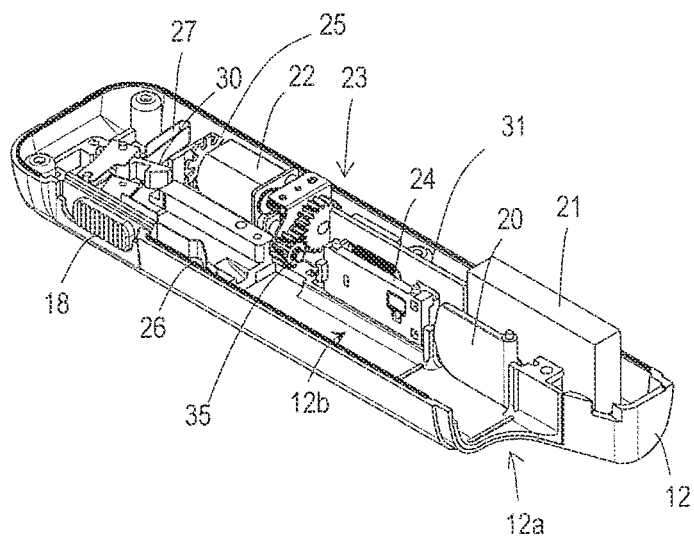
(b)
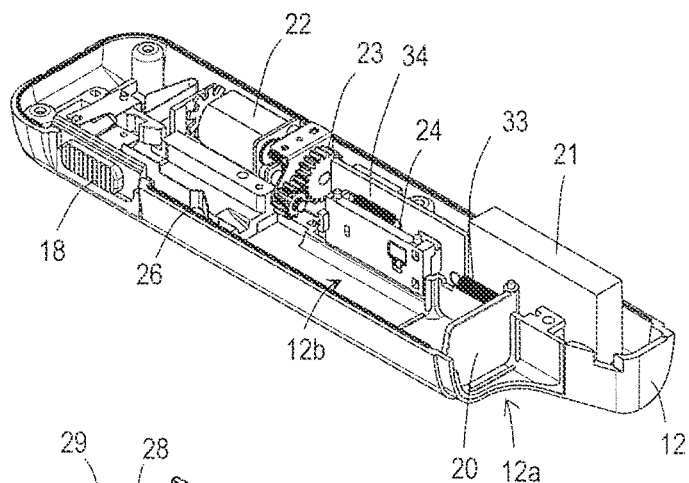
(c)
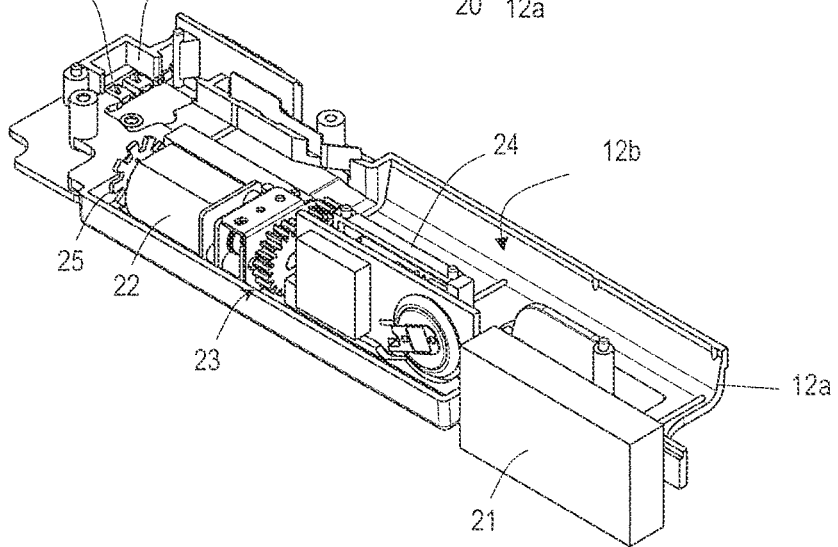

FIG.12
(a)
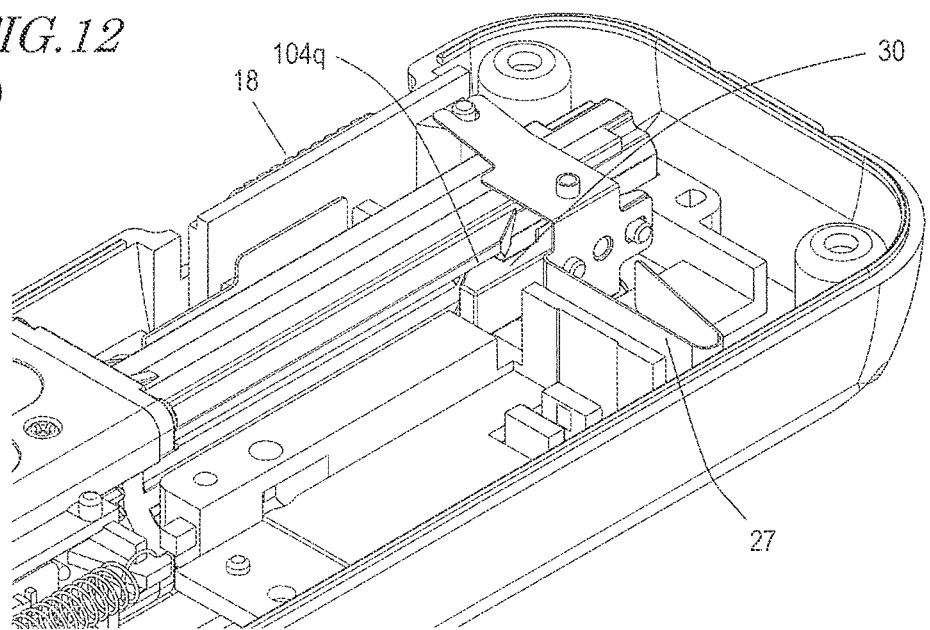
(b)
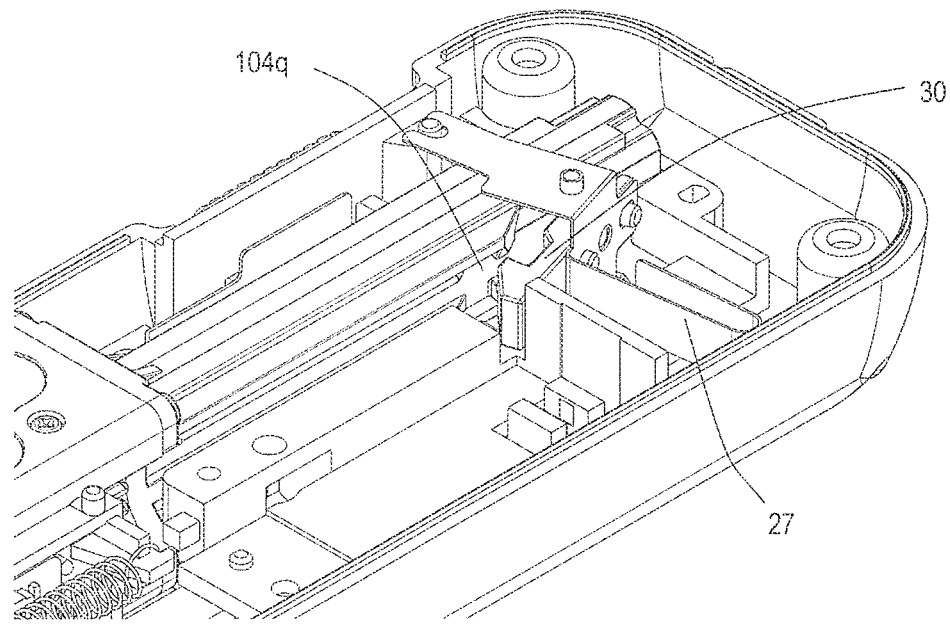

FIG.13
(a)
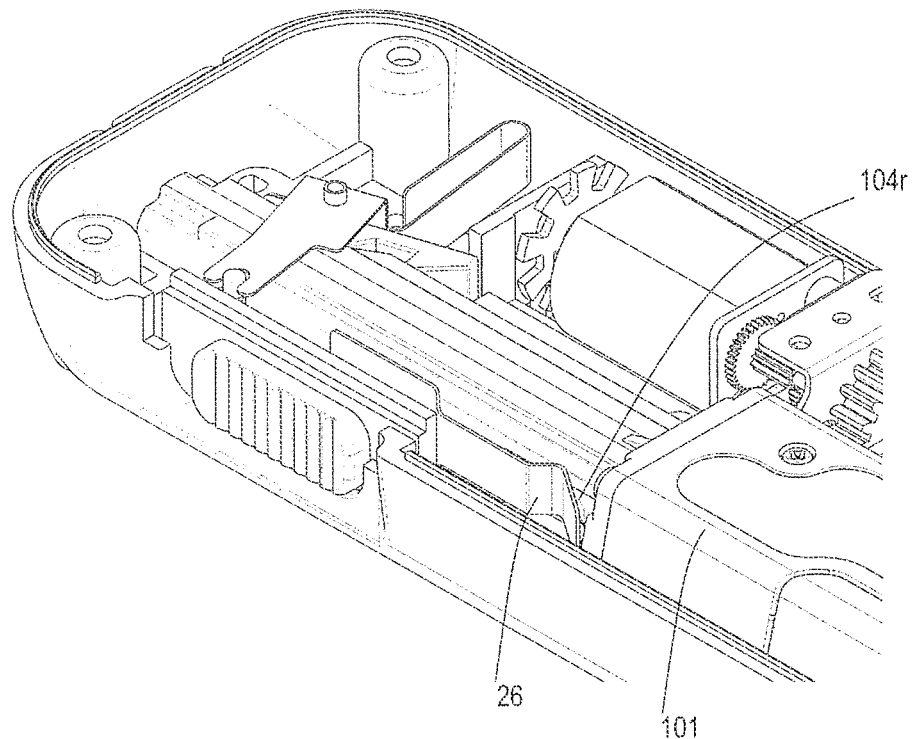
(b)
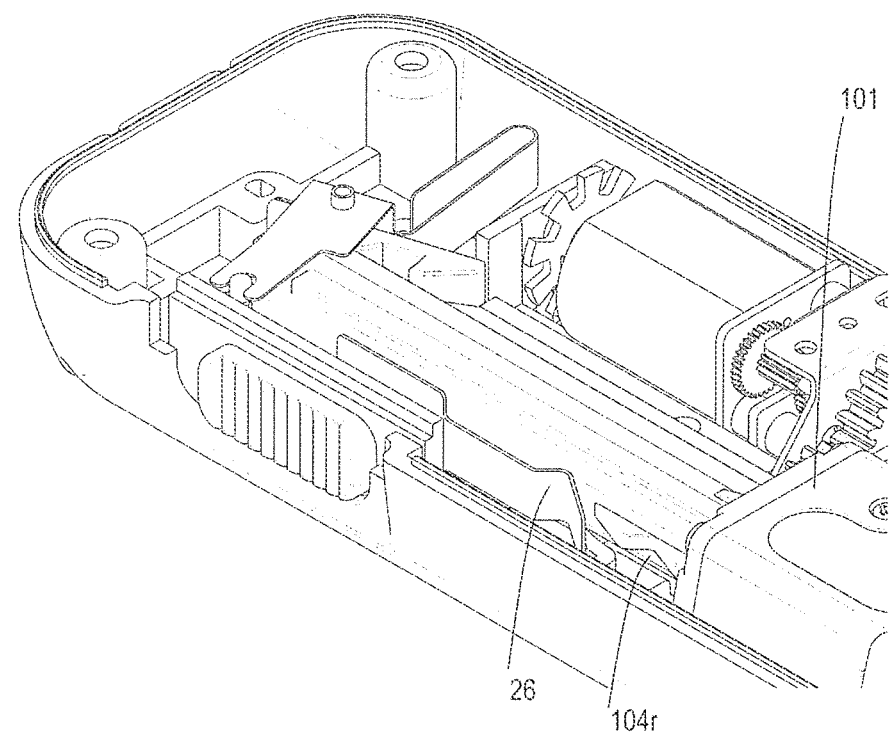

FIG.14
(a)
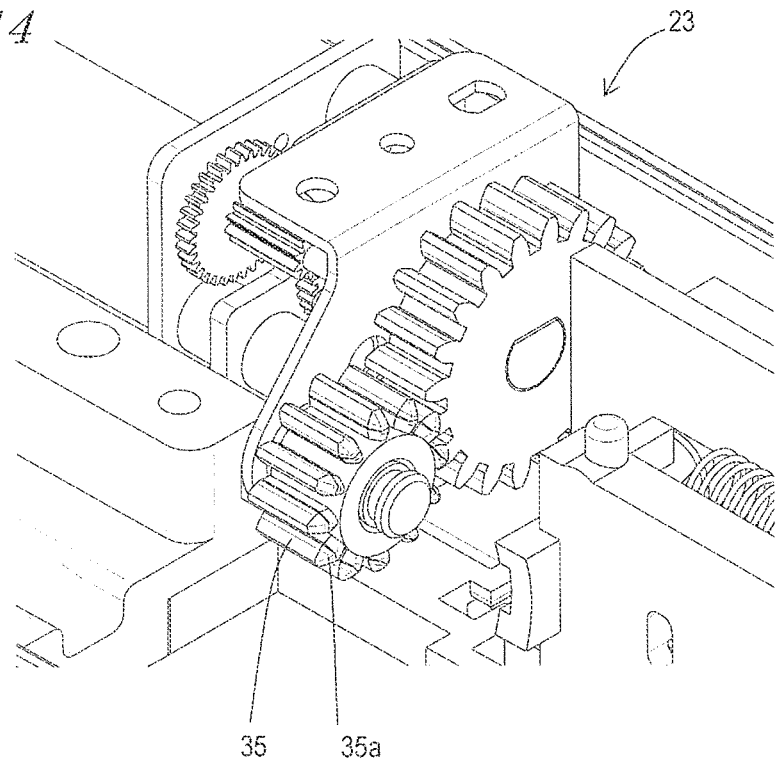
35  35a
(b)
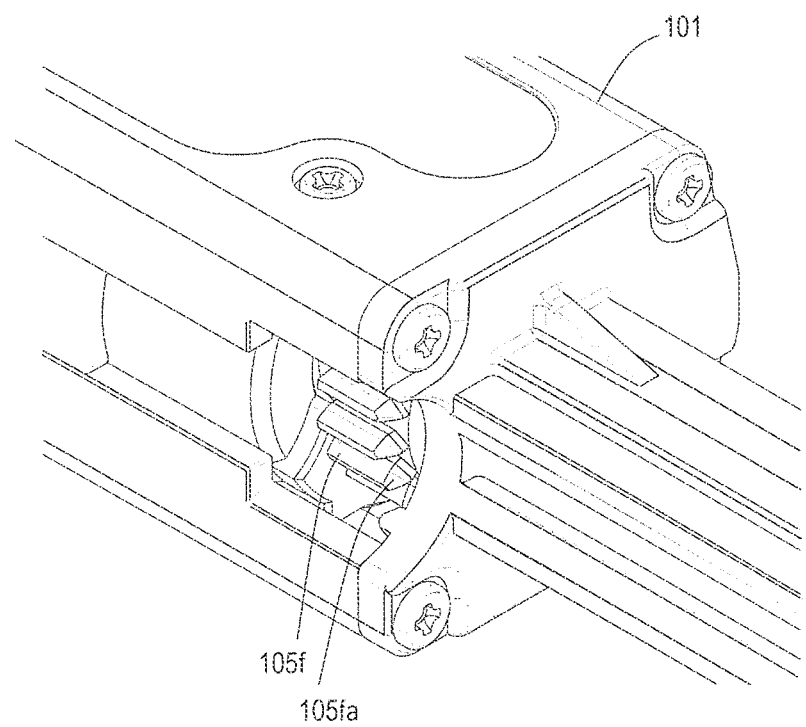
105f
105fa

FIG.18
(a)
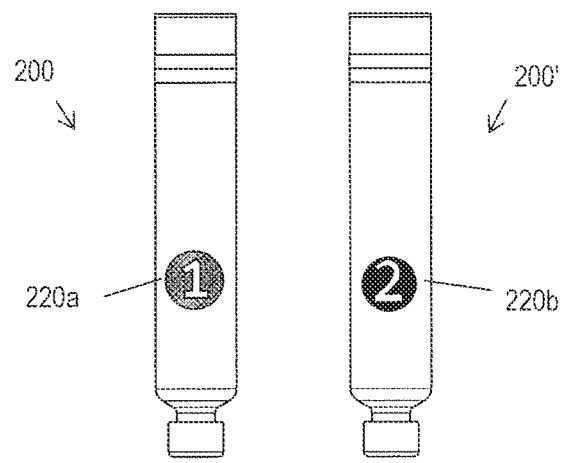
(b)
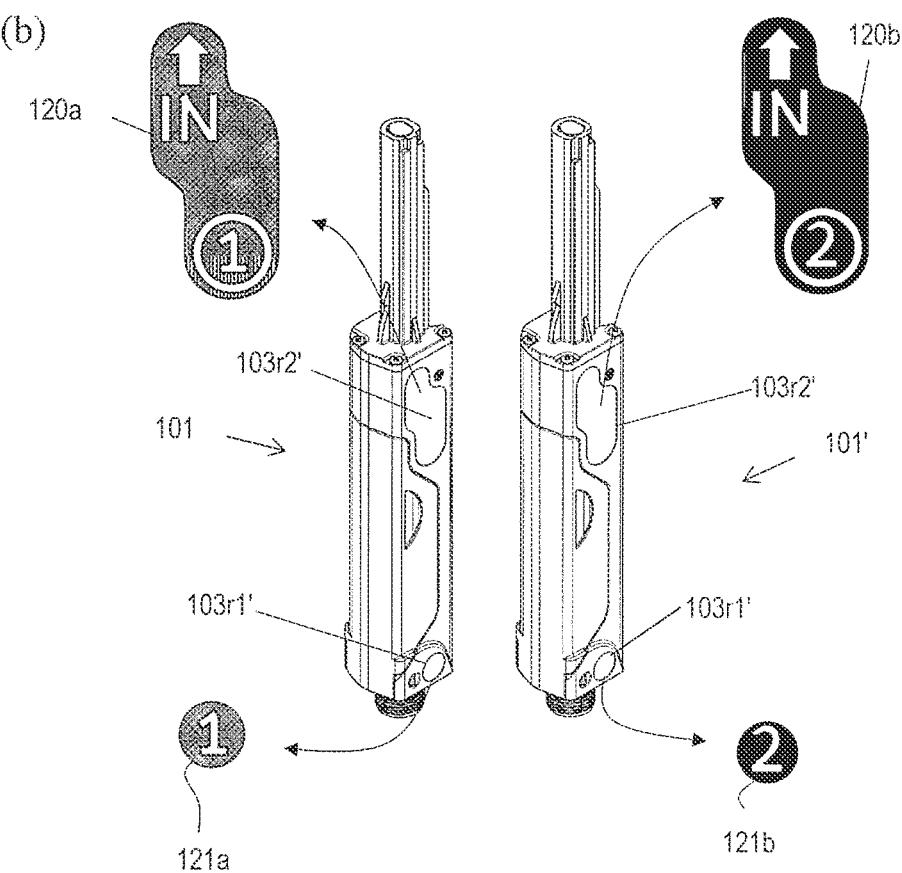

FIG.29
(a) 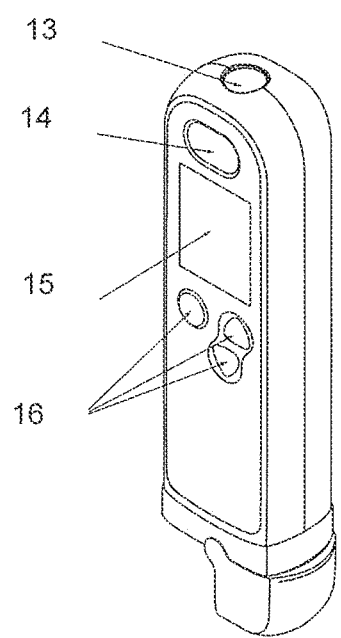
(b) 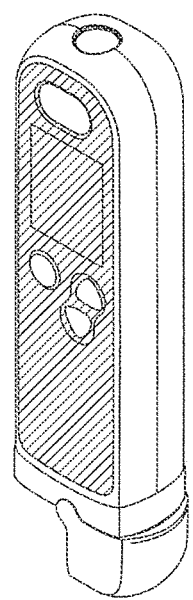

DRUG INJECTION DEVICE

CROSS-REFERENCE OF RELATED APPLICATIONS

This application is a Divisional application of U.S. patent application Ser. No. 15/779,005, filed on May 24, 2018, which is a U.S. National Phase under 35 U.S.C. § 371 of International Patent Application No. PCT/JP2016/087101 filed on Dec. 13, 2016, which in turn claims the benefit of Japanese Application No. 2015-252431 filed on Dec. 24, 2015, the disclosures of which Applications are incorporated by reference herein.

TECHNICAL FIELD

The present application relates to a drug injection device, a cartridge adapter and a drug injection system for inject medical drugs.

BACKGROUND ART

Patients suffering from particular diseases in some cases need to receive an injection of a drug such as insulin, growth hormone, or the like, a plurality of times a day. In order for the patients to inject such a drug by themselves, drug injection devices disclosed in Patent Document No. 1 and Patent Document No. 2 have been realized, for example.

The drug injection devices disclosed in these documents each include a main body and a drug cartridge that can be loaded in the main body, and a piston provided in the main body is used to push in the plunger of the drug cartridge so as to inject the drug.

The dosage, etc., of a drug are typically unique to the patient and the drug used for the patient. Therefore, each drug injection device and each type of a drug cartridge have a one-to-one correspondence, and for a certain drug cartridge, a drug injection device dedicated for the drug cartridge is used.

Therefore, when it is necessary to inject a plurality of types of drugs, injections are performed by using a plurality of drug injection devices in accordance with the number of drugs.

CITATION LIST

Patent Literature

Patent Document No. 1: Japanese Laid-Open Patent Publication No. 2012-50847
Patent Document No. 2: Japanese National Phase PCT Laid-Open Publication No. 2014-516634

SUMMARY OF INVENTION

Technical Problem

For the purpose of convenience, etc., there is a need to realize a drug injection device that accommodates a plurality of drug cartridges.

A non-limiting exemplary embodiment of the present application provides a drug injection device, a cartridge adapter and a drug injection system that accommodate a plurality of types of drug cartridges.

Solution to Problem

A cartridge adapter of the present disclosure includes: a cartridge holder having a space that can accommodate therein a drug cartridge, the drug cartridge including a cylinder having a tubular internal space extending in a longitudinal direction, a gasket supported in the internal space so as to be movable in the longitudinal direction, and a drug held in the internal space; a piston that moves the gasket in the longitudinal direction in the internal space of the cylinder; a piston guide that to movably supports the piston and connected to the cartridge holder; and a piston driving mechanism that drives the piston in the longitudinal direction.

Advantageous Effects of Invention

According to the present disclosure, there are provided a drug injection device, a cartridge adapter and a drug injection system that accommodate a plurality of types of drug cartridges.

BRIEF DESCRIPTION OF DRAWINGS

FIG. 2(a) is a perspective view showing a drug injection system 100 where a cartridge adapter 101 is loaded in a drug injection device 11, as seen from a different angle from FIG. 1, and FIG. 2(b) is a perspective view showing the drug injection system 100 with the cartridge adapter removed.

FIGS. 8(a) and 8(b) are perspective views showing an internal structure of the drug injection device 11 where a casing 12 is divided in a horizontal direction and removed, and FIG. 8(c) is a perspective view showing an internal structure of the drug injection device 11 that is located on the opposite side of the divided casing 12.

FIGS. 12(a) and 12(b) are perspective views showing a lock mechanism on an enlarged scale.

FIGS. 13(a) and 13(b) are perspective views showing an anti-slip mechanism on an enlarged scale.

FIGS. 14(a) and 14(b) are perspective views showing, on an enlarged scale, the vicinity of a piston gear 105 of the cartridge adapter 101 and a drive gear 35 of the drug injection device 11.

FIGS. 18(a) and 18(b) show examples of visual features provided on drug cartridges 200 and 200' and cartridge adapters 101 and 101'.

FIGS. 29(a) and 29(b) are a reference diagram showing names of various portions of the drug injection device 11 shown in FIG. 27 and a reference diagram showing a transparent portion thereof, respectively.

DESCRIPTION OF EMBODIMENTS

Figure 1:
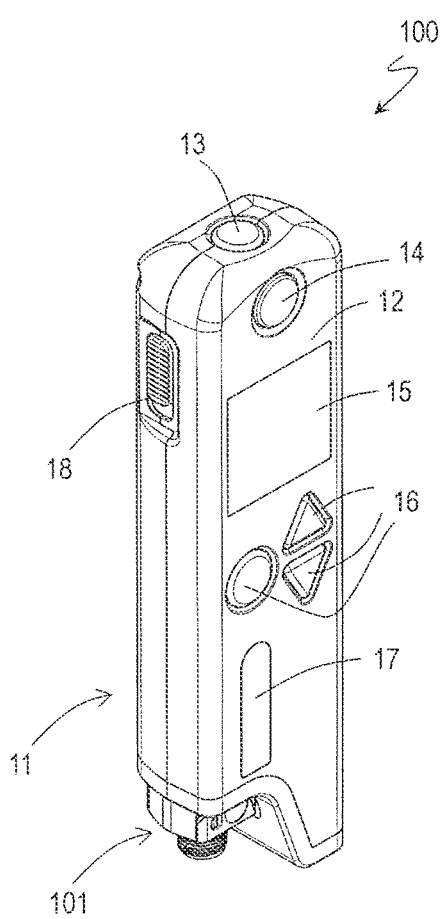
FIG. 1 is a perspective view showing an external appearance of an example of a drug injection system of the present embodiment.

With drug injection devices of the application described above, a drug filling one drug cartridge is injected over a plurality of iterations. Therefore, where different drugs are injected, one drug injection device will be used while switching between two or more drug cartridges that are being used.

Since the amount of drug to be inject may not be equal between a plurality of different drug cartridges, the piston for pushing a drug out of a drug cartridge needs to be retracted from the drug cartridge every time a drug cartridge is replaced with another. As a result, when switching between drug cartridges, it takes time before an injection is ready to be given. Also, in order to inject the correct amount, it is necessary, every time a drug cartridge is replaced with another, to correctly set the starting point of the piston, etc., and to accurately control the movement of the piston. Moreover, moving the piston every time replacement is done increases the consumption of the battery provided in the drug injection device.

In view of these problems, the present inventors have arrived at a novel drug injection device, a cartridge adapter, a drug injection system and a method for controlling a drug injection system that are capable of accommodating a plurality of types of drug cartridges.

The drug injection device, the cartridge adapter, the drug injection system and the method for controlling a drug injection system of the present disclosure are outlined below.

[Item 1] A cartridge adapter including:
a cartridge holder having a space that can accommodate therein a drug cartridge, the drug cartridge including a cylinder having a tubular internal space extending in a longitudinal direction, a gasket supported in the internal space so as to be movable in the longitudinal direction, and a drug held in the internal space;
a piston that moves the gasket in the longitudinal direction in the internal space of the cylinder;
a piston guide that movably supports the piston and connected to the cartridge holder; and
a piston driving mechanism that drives the piston in the longitudinal direction.

[Item 2] The cartridge adapter of item 1, the piston driving mechanism including:
a male thread located on an outer circumference of the piston; and
a piston gear having an inner surface on which a female thread that meshes with the male thread is located and an outer surface on which a gear is located.

[Item 3] The cartridge adapter of item 1, further including first identification information in accordance with a type of the drug cartridge to be accommodated therein.

[Item 4] The cartridge adapter of item 3, wherein the first identification information is a cutout or a projection located on a portion of an outer shape of the cartridge adapter.

[Item 5] The cartridge adapter of any one of items 1 to 4, wherein:
the drug cartridge has a unique visual feature in accordance with the drug; and
the cartridge adapter has a visual feature that is similar to the unique visual feature of the drug cartridge.

[Item 6] The cartridge adapter of item 5, wherein the visual feature is at least one selected from a color, a pattern and a symbol.

[Item 7] The cartridge adapter of any one of items 1 to 6, wherein:
the drug cartridge has unique second identification information in accordance with the drug; and
the cartridge holder has an opening that exposes therethrough at least a portion of the second identification information of the drug cartridge.

[Item 8] The cartridge adapter of item 7, wherein the second identification information is a colored region provided with a unique color.

[Item 9] The cartridge adapter of item 7, wherein in a state in which the drug cartridge that is unused is accommodated in the cartridge holder, the piston is movable between a first, most retracted position at which there is a predetermined interval between a distal end of the piston and the gasket, and a second position at which the distal end of the piston and the gasket are in contact with each other and at which the gasket is inserted farthest into the cylinder.

[Item 10] The cartridge adapter of item 9, further including:
a slide member that moves in the longitudinal direction as the piston moves from the first position to a third position at which the piston is in contact with the gasket, wherein:
the slide member has a shade portion that covers a portion of the opening of the cartridge holder and a slit that is located in the shade portion; and
as the slide member moves in the opening, the slit scans the colored region of the drug cartridge in the longitudinal direction.

[Item 11] The cartridge adapter of item 10, further including:
a spring that forces the slide member toward one end of the cylinder of the drug cartridge, wherein:
in a state in which the slide member is in contact with the one end of the cylinder, the spring forces the cylinder toward the other end of the cylinder.

[Item 12] The cartridge adapter of item 11, wherein:
the cartridge holder further includes a main body having an opening through which the drug cartridge is inserted, and a lid that is movable so as to open and close the opening; and
in a state in which the slide member is in contact with the one end of the cylinder, the slide member is in contact with a portion of the lid and locks the lid.

[Item 13] A drug injection device including:
a casing having an adapter space in which a cartridge adapter of item 1 can be loaded, and an opening that communicates with the adapter space;
a driver that is in engagement with the piston driving mechanism of the cartridge adapter loaded in the adapter space and transmit a driving force;
an arithmetic circuit that controls the driver; and
a memory.

[Item 14] The drug injection device of item 13, the piston driving mechanism of the cartridge adapter including:
a male thread located on an outer circumference of the piston; and
a piston gear having an inner surface on which a female thread that meshes with the male thread is located and an outer surface on which a gear is located, wherein:
the driver includes a motor and a drive gear that rotates by receiving a driving force from the motor; and
in a state in which the cartridge adapter is loaded in the adapter space, the drive gear of the driver meshes with the piston gear of the piston driving mechanism.

[Item 15] The drug injection device of item 13, further including:
a flap that is movable so as to open and close the opening of the casing, wherein:
when the cartridge adapter is loaded, the flap opens the opening; and
when the cartridge adapter is pulled out, the flap shuts the opening.

[Item 16] The drug injection device of item 13, further including:
a loading detector and a first identification information detector, wherein:
the cartridge adapter further includes first identification information in accordance with a type of the drug cartridge to be accommodated therein;
the loading detector detects loading of the cartridge adapter; and
the first identification information detector detects the first identification information of the drug cartridge.

[Item 17] The drug injection device of item 16, further including:
a display, wherein:
based on a detection result of the first identification information detector, the arithmetic circuit causes the display to display a feature that is similar to the visual features of the drug cartridge and the cartridge adapter.

[Item 18] The drug injection device of item 16, wherein:
the memory stores information of an injection schedule; and
based on the information of the injection schedule and the detection results of the loading detector and the first identification information detector, the arithmetic circuit causes the display to produce a display that is similar to the visual feature in accordance with a type of a drug that should be loaded, if no cartridge adapter is loaded or if a cartridge adapter of a drug that is not according to the injection schedule is loaded.

[Item 19] The drug injection device of item 13, further including a lock mechanism, the lock mechanism including an engagement member that is in engagement with the cartridge adapter placed in the adapter space, and a release lever that releases the engagement between the engagement member and the cartridge adapter.

[Item 20] The drug injection device of item 19, further including an anti-slip mechanism that a is in engagement with the cartridge adapter so as to prevent the cartridge adapter from slipping off the adapter space in a state in which the lock mechanism is released.

[Item 21] The drug injection device of item 13, further including:
a second identification information detector, wherein:
the drug cartridge has unique second identification information in accordance with the drug; and
the second identification information detector detects the second identification information of the drug cartridge.

[Item 22] The drug injection device of item 21, wherein:
the second identification information is a colored region provided with a color that is unique to the drug; and
the second identification information detector detects the color of the colored region of the drug cartridge.

[Item 23] The drug injection device of item 22, wherein:
the second identification information detector includes a base, and a photodetector and a light emitting element located on the base;
the cartridge holder has an opening that exposes therethrough at least a portion of the colored region of the drug cartridge;
in a state in which the drug cartridge that is unused is accommodated in the cartridge holder, the piston is movable between a first, most retracted position at which there is a predetermined interval between a distal end of the piston and the gasket, and a second position at which the distal end of the piston and the gasket are in contact with each other and at which the gasket is inserted farthest into the cylinder;
the cartridge adapter further includes a slide member that moves in the longitudinal direction as the piston moves from the first position to a third position at which the piston is in contact with the gasket;
the slide member has a shade portion that covers a portion of the opening of the cartridge holder and a slit that is located in the shade portion;
as the slide member moves, the slit scans the colored region of the drug cartridge in the longitudinal direction; and
as the base of the second identification information detector moves in the longitudinal direction together with the slide member of the cartridge adapter, the second identification information detector detects the color based on light that enters through the slit of the slide member.

[Item 24] A drug injection system including:
a cartridge adapter of item 1; and
a drug injection device of item 13.

An example of a drug injection system of the present embodiment will now be described in detail with reference to the drawings. The drug injection system to be described below is an example embodiment. The embodiment is not limited to the configuration shown below, but various modifications can be made thereto. In the figures to be referred to in the following description, those reference signs that are not referred to in the description may be omitted for the sake of simplicity.

(Configuration of Drug Injection System)

[External Appearance of Drug Injection System]

FIG. 1 is a perspective view showing an external appearance of an example of a drug injection system of the present embodiment. As shown in FIG. 1, a drug injection system 100 includes a drug injection device 11 and a cartridge adapter 101. The cartridge adapter 101 accommodates a drug cartridge therein as will be described below. FIG. 1 shows a state in which the cartridge adapter 101 is loaded in the drug injection device 11.

The drug injection device 11 includes a casing 12 that has an adapter space therein where the cartridge adapter 101 is accommodated. The drug injection device 11 includes, provided on the casing 12, various buttons for operating the drug injection device 11 and a display 15 for displaying the state of the drug injection device 11 and displaying instructions to the operator. For example, as shown in FIG. 1, the casing 12 is provided with a power button 13, an injection (drug administration) button 14, an operation button 16, etc. The power button 13 is used for turning on and off the drug injection device 11, for example. The injection button 14 is used for injecting a drug. The operation button 16 is used, for example, for moving an icon displayed on the display so as to select a condition displayed on the display 15 or to change the numerical value displayed on the display. It is also used for confirming the selected condition or numerical value. The display 15 is a liquid crystal display panel, an organic EL panel, or the like, for example. The display 15 may be a touch panel, and at least one of the functions of the power button 13, the injection button 14 and the operation button 16 may be realized by the touch panel.

The drug injection device 11 may include a lock release lever 18 provided on the casing 12. The lock release lever 18 is used for removing the cartridge adapter 101. The structure of the lock release lever 18 will be described below in detail. The drug injection device 11 may include a check window 17 provided on the casing 12. The check window 17 may be an opening in the casing 12, or may be an opening in the casing 12 and a member made of a transparent material such as a glass or a resin provided in the opening. The check window 17 corresponds to the position of the cartridge adapter 101 as loaded, and a portion of the loaded cartridge adapter 101 can be seen through the check window 17. Therefore, even when the power of the drug injection device 11 is OFF and no information is displayed on the display 15, the operator can check whether the cartridge adapter 101 is loaded or not loaded.

Note that although not shown in the figures, the drug injection device 11 may further include a sound-generating device such as a buzzer 43 (FIG. 9) or a loud speaker. It is possible to provide a higher level of operability by giving an alarm from a buzzer, a loud speaker, or the like, or by giving a sound, or the like, that indicates that one of the various buttons described above has been pressed and the input has been accepted.

FIG. 2(a) is a perspective view showing the drug injection system 100 where the cartridge adapter 101 is loaded in the drug injection device 11, as seen from a different angle from FIG. 1. As shown in FIG. 2(a), a needle attachment portion 102, to which a needle is to be attached, is provided at the distal end of the cartridge adapter 101. In a state in which the cartridge adapter 101 is correctly loaded in the drug injection device 11, the needle attachment portion 102 is projecting from the casing 12. A needle to be inserted into the skin of the patient is attached to the needle attachment portion 102.

FIG. 2(b) is a perspective view showing the drug injection system 100 with the cartridge adapter removed therefrom. The casing 12 has an opening 12a that communicates with the adapter space in which the cartridge adapter 101 is accommodated. With the cartridge adapter 101 removed, the opening 12a is shut by a flap 20. Thus, with the cartridge adapter 101 removed, it is possible to prevent a foreign matter from entering the inside of the casing 12 through the opening 12a.

[Cartridge Adapter 101]

Figure 3:
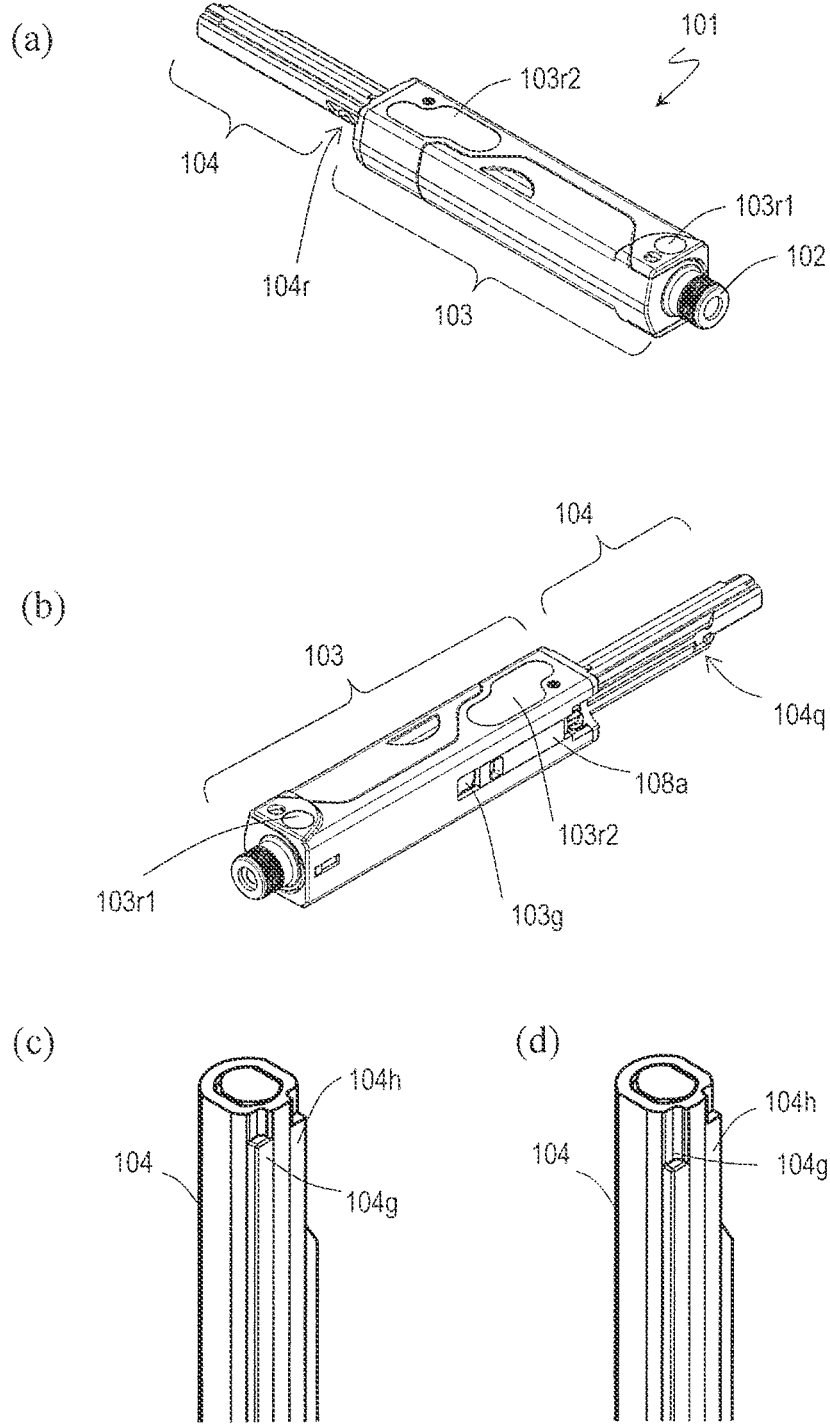
FIGS. 3(a) and 3(b) are perspective views showing an example of an external appearance of the cartridge adapter 101.
FIGS. 3(c) and 3(d) are perspective views showing one end of a piston guide portion 104 in the longitudinal direction on an enlarged scale.

FIGS. 3(a) and 3(b) are perspective views showing an example of an external appearance of the cartridge adapter 101. The cartridge adapter 101 includes the needle attachment portion 102, a cartridge holder 103 and the piston guide portion 104. The cartridge holder 103 has an internal space in which the drug cartridge is accommodated. The cartridge holder 103 and the piston guide portion 104 each have a shape that is elongated in the longitudinal direction of the drug cartridge to be accommodated. One end of the cartridge holder 103 is connected to one end of the piston guide portion 104. The piston guide portion 104 has a space therein for guiding the movement of a piston to be described below.

The cartridge holder 103 has a region 103r1 and a region 103r2 on the outer surface thereof for displaying a visual feature in accordance with the type of the drug cartridge accommodated therein. The visual feature is displayed on the region 103r1 and the region 103r2. The visual feature is presented primarily to the operator. The visual feature will be described below in detail.

The cartridge adapter 101 is provided with a depressed portion 104r for preventing the cartridge adapter 101 from easily slipping off the drug injection device 11 by virtue of gravity, etc., in a state in which the lock release lever 18 described above is released. While the depressed portion 104r is provided on the outer surface of the piston guide portion 104 in FIG. 3(a), it may be provided on the cartridge holder 103. Another depressed portion 104q is provided on the outer surface of the piston guide portion 104 on the opposite side from the depressed portion 104r.

FIGS. 3(c) and 3(d) are perspective views showing, on an enlarged scale, one end of the piston guide portion 104 in the longitudinal direction. Loading information 104h and first identification information 104g are provided at an end portion of the cartridge adapter 101 as a whole where the needle attachment portion 102 is absent, i.e., at an end portion of the piston guide portion 104. The loading information 104h is used for detecting whether or not the cartridge adapter 101 is loaded in the drug injection device 11, and the loading information 104h is presented to the drug injection device 11 in a state in which the cartridge adapter 101 is located in the drug injection device 11. The drug injection device 11 includes a loading detector that is compatible with the configuration of the loading information 104h. In the example shown in FIGS. 3(c) and 3(d), the loading information 104h is a protruding portion provided on the outer shape of the cartridge adapter 101. In this case, a microswitch can be used as the loading detector, for example, and when the microswitch is pressed by the protruding portion, the microswitch is turned ON so that the loading detector outputs a signal indicating the loading.

The first identification information 104g is used for identifying the type of the cartridge adapter 101. The first identification information 104g is also presented to the drug injection device 11 in a state in which the cartridge adapter 101 is located in the drug injection device 11, and the drug injection device 11 includes a first identification information detector that is compatible with the configuration of the first identification information 104g. In the examples shown in FIGS. 3(c) and 3(d), the first identification information 104g is a depressed portion and a protruding portion, respectively, provided on the outer shape of the cartridge adapter 101. Based on whether the first identification information 104g is a depressed portion or a protruding portion, information of two types of drug cartridges can be presented to the drug injection device 11. Also in this case, a microswitch, for example, can be used as the first identification information detector.

The loading information 104h and the first identification information 104g are not limited to structural shapes as in the example described above, but may be any of various information. For example, the loading information 104h and the first identification information 104g may each be a conductor (region), a magnetic force (magnetic region) or an optical characteristic provided on the outer surface of the cartridge adapter 101. Specifically, the loading information 104h and the first identification information 104g may be provided based on whether or not a conductor is present, whether or not a magnet is present, or whether a shaded region or a reflective region is present. In this case, the loading and the type of the cartridge adapter may be determined by detecting a conductivity, a magnetic force and a light transparency. The position at which the loading information 104h and the first identification information 104g are provided is not limited to one end of the piston guide portion 104, but may be provided at any other location.

With the drug injection system 100, each cartridge adapter 101 uniquely corresponds to a drug cartridge 200 accommodated therein, and a certain drug cartridge 200 is accommodated in a cartridge adapter 101 dedicated thereto. However, a cartridge adapter 101 for a certain drug can accommodate a different drug cartridge 200. In such a case, it is not possible to determine whether a correct drug is to be inject based only on the first identification information 104g of the cartridge adapter 101 described above. As will be described below in detail, when a new (unused) drug cartridge 200 is inserted in the cartridge adapter 101, the drug injection device 11 first determines whether or not the drug cartridge 200 and the cartridge adapter 101 correctly correspond to each other. Therefore, as shown in FIG. 3(b), the cartridge adapter 101 has an opening 103g provided in the cartridge holder 103. The opening 103g exposes therethrough a portion of the external appearance of the accommodated drug cartridge 200. As will be described below, the external appearance of the drug cartridge includes second identification information 205 (FIG. 4(a)) that is unique to the drug, and at least a portion of the second identification information is exposed through the opening 103g.

While the visual feature is presented primarily to the operator, the second identification information is used primarily for the detection by the drug injection device 11. For example, the second identification information may be a colored region provided with a color that is unique to the drug or may be a one-dimensional or two-dimensional barcode that corresponds to a numerical value unique to the drug. It may also be an IC tag such as an RFID. The second identification information is provided on the outer surface of a cylinder 201, for example. When the drug cartridge 200 is accommodated in the cartridge adapter 101, if there is no particular limitation on the angle of the drug cartridge 200 about the central axis that extends along the longitudinal direction of the drug cartridge 200, the second identification information may be provided in a band shape across the entire circumference of the outer surface of the cylinder 201 so that the second identification information is exposed through the opening 103g, irrespective of the angle at which the drug cartridge 200 is accommodated. There may be one or more colored band regions.

Figure 4:
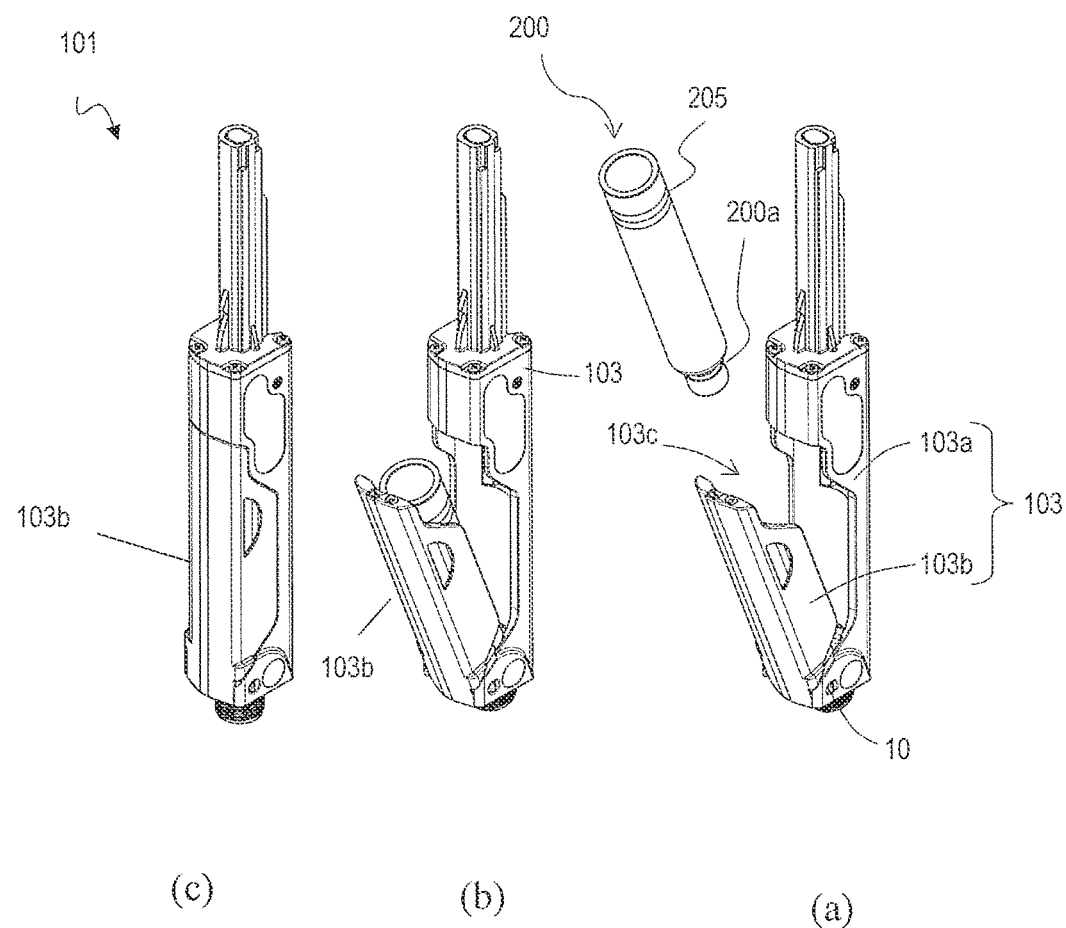
FIGS. 4(a) to 4(c) are perspective views showing three states where a drug cartridge 200 is being loaded in the cartridge adapter 101.

FIGS. 4(a) to 4(c) are perspective views showing three states where the drug cartridge 200 is being loaded in the cartridge adapter 101. As shown in FIG. 4(a), the cartridge holder 103 of the cartridge adapter 101 includes a main body 103a having an opening 103c through which the drug cartridge 200 is inserted, and a lid 103b. The lid 103b is allowed to pivot about a pivot axis, and can open and close the opening 103c by pivoting. The lid 103b is provided with side surfaces, thereby forming a space 103f in which the drug cartridge 200 is accommodated.

With the lid 103b open, the drug cartridge 200 is inserted into the space 103f of the lid 103b, with a distal end 200a, where a needle is attached, facing down, i.e., inserted from the distal end 200a. As shown in FIG. 4(b), by pivoting the lid 103b about the pivot axis toward the main body 103a, the lid 103b closes the opening 103c, and the drug cartridge 200 is accommodated in the cartridge adapter 101. By the reverse procedure, the drug cartridge 200 can be taken out of the cartridge adapter 101.

Figure 5:
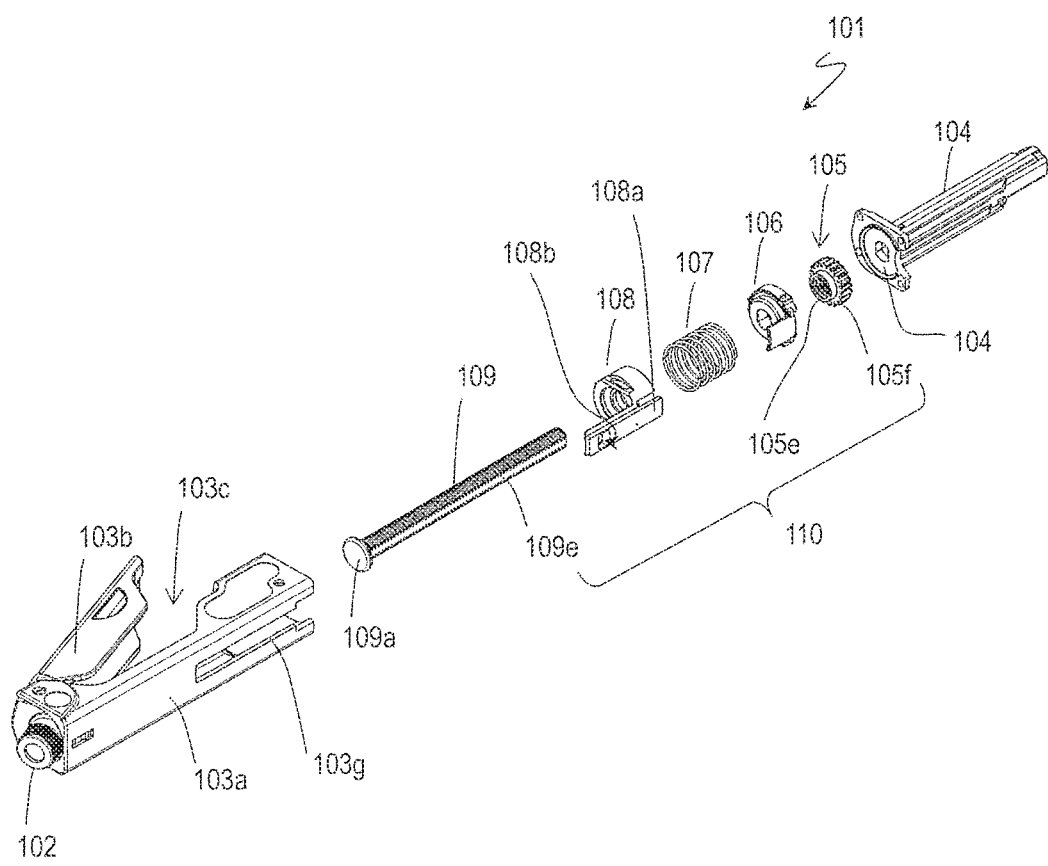
FIG. 5 is an exploded perspective view showing components of the cartridge adapter 101.

FIG. 5 is an exploded perspective view showing components of the cartridge adapter 101. The cartridge adapter 101 includes the cartridge holder 103, the piston guide portion 104, a piston gear 105, a gear retainer 106, a spring 107, a slide member 108 and the piston 109.

The piston guide portion 104 has a hole 104a for slidably supporting the piston. The piston gear 105 is sandwiched, and rotatably supported, between the piston guide portion 104 and the gear retainer 106. The gear retainer 106 has a through hole through which the piston 109 is inserted. A female thread 105e is provided on the inner surface of the piston gear 105. A gear 105f is provided on the outer surface.

The slide member 108 has a shade portion 108a, and a slit 108b provided in the shade portion 108a. It also has a through hole through which the piston is inserted.

The piston 109 has a rod shape, and a male thread 109e is provided on the outer surface. The male thread 109e is provided with a flat portion 109f extending along the longitudinal direction. A tip 109a for pushing a gasket 202 of the drug cartridge 200 is located at one end of the piston 109.

The slide member 108, the spring, the gear retainer 106, the piston gear 105 and the piston guide portion 104 are inserted in this order from the end of the piston 109 where the tip 109a is absent. In this state, the piston guide portion 104 is attached to one end of the cartridge holder 103.

In the cartridge adapter 101, the male thread 109e of the piston 109 is meshed with the female thread 105e of the piston gear 105. As the piston gear 105 is rotated by the torque transmitted from the drug injection device 11, the torque is transmitted to the piston 109 by the meshing between the female thread 105e and the male thread 109e. Thus, a force acts in the direction of rotating the piston 109. However, the male thread 109e of the piston 109 is provided with the flat portion 109f, and the hole of the gear retainer 106 or the piston guide portion 104, for example, is provided with a restricting surface that is in contact with the flat portion 109f. Therefore, the piston 109 is moved in the longitudinal direction while the rotation of the piston 109 itself is prevented. That is, the torque received by the piston gear 105 is converted to a driving force for driving the piston 109 in the longitudinal direction. Thus, the piston gear 105 and the male thread 109e of the piston 109 together form a piston driving mechanism 110. The piston driving mechanism 110 is not limited to this configuration, and it may be realized by a combination of mechanical elements known in the art for converting rotary motion to reciprocating motion, for example. For example, the piston driving mechanism 110 may be implemented by providing a rack on the side surface of the piston 109 so that the drive gear of the drug injection device 11 meshes directly with the rack, or the cartridge adapter 101 may be further provided with a pinion gear.

[Drug Cartridge 200]

Figure 6:
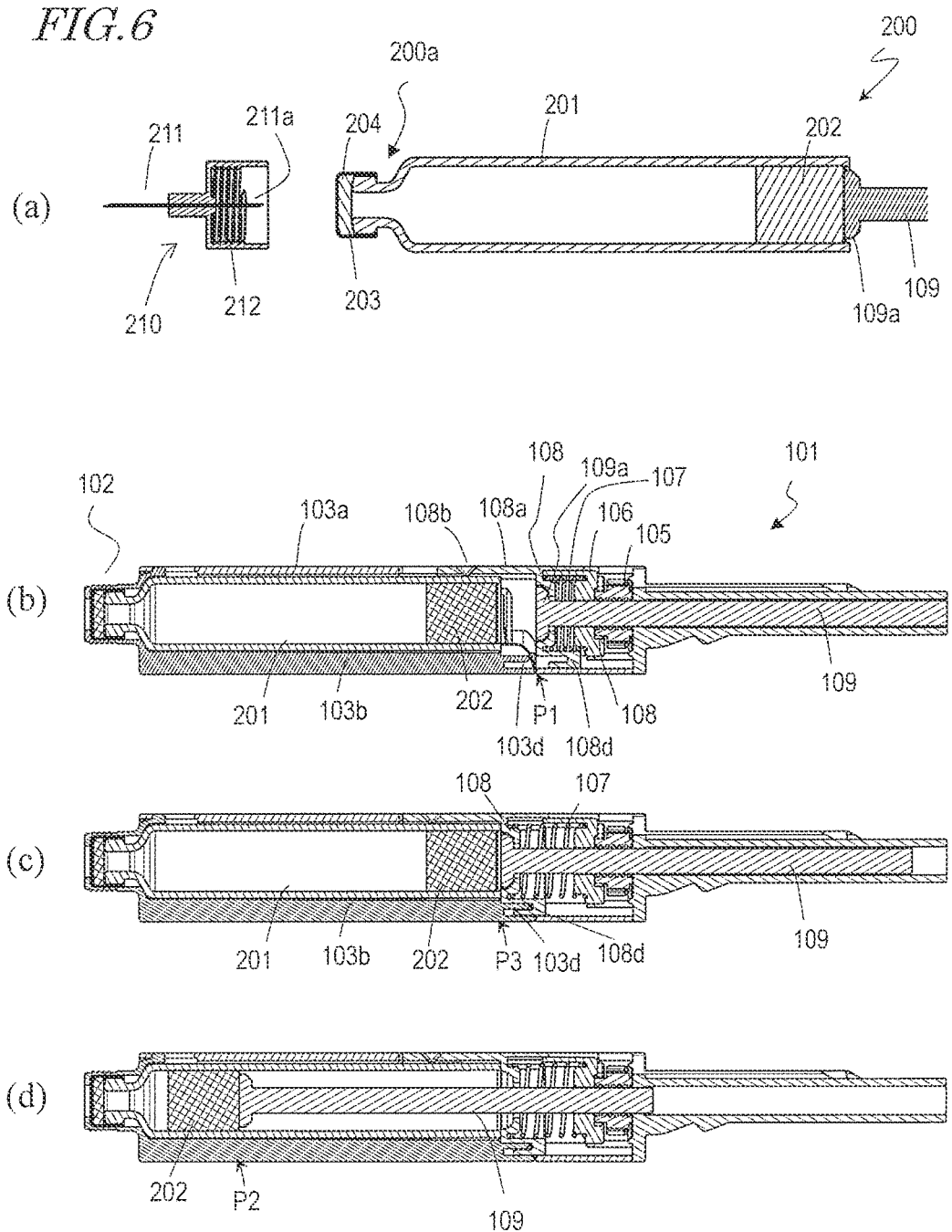
FIG. 6(a) is a cross-sectional view showing a structure of the drug cartridge 200.
FIGS. 6(b) to 6(d) are cross-sectional views showing the operation of the cartridge adapter 101.

Referring to FIG. 6(a), the structure of the drug cartridge 200 will be described. As shown in FIG. 6(a), the drug cartridge 200 includes the cylinder 201, the gasket 202, a cap 203 and a packing 204. The cylinder 201 has a tubular internal space extending in the longitudinal direction, with the distal end 200a being tapered. The gasket 202 is located in the internal space of the cylinder 201, and the gasket 202 is allowed to slide in the cylinder 201. The distal end 200a is sealed by the packing 204, and is further covered by the cap 203. A drug is held in the internal space closed by the gasket 202. As shown in FIG. 6(a), the tip 109a of the piston 109 is in contact only with the gasket 202 but not with the cylinder 201.

An injection needle 210 has a cap 212 and a needle 211. It is attached to the needle attachment portion 102 of the cartridge adapter 101. The rear needle of the needle 211 is inserted into the cap 203 and the packing 204 of the drug cartridge 200.

[Operation of Cartridge Adapter 101]

Referring to FIG. 6(b) to FIG. 6(d), the operation of the cartridge adapter 101 will be described. When accommodating the drug cartridge 200 in the cartridge adapter 101, the piston 109 is at the most retracted position so as not to interfere with the drug cartridge 200.

At this point, the distal end of the tip 109a of the piston 109 is at position P1 and is at a predetermined distance from the end portion of the drug cartridge 200. The position of the piston, as used hereinbelow, refers to the position of the distal end of the tip 109a. Since the piston 109 is meshed with the piston gear 105, the piston 109 does not move in the longitudinal direction unless the piston gear 105 rotates. In this state, the spring 107 is compressed, and the slide member 108 is forced toward the drug cartridge by the force of the spring 107. However, since the tip 109a of the piston 109 is larger than the through hole of the slide member 108, the slide member 108 cannot move toward the drug cartridge 200 because of the tip 109a of the piston.

FIG. 6(c) shows a state in which the piston 109 has been moved toward the drug cartridge 200 by the rotation of the piston gear 105 so that the distal end of the tip 109a is in contact with the gasket 202. At this point, the distal end of the tip 109a of the piston 109 is at position P3.

The slide member 108 moves toward the drug cartridge 200, by the amount by which the tip 109a has moved, by the force of the spring 107. As a result, the slide member 108 comes into contact with the end portion of the cylinder 201 of the drug cartridge 200. In this state, the spring 107 is not fully restored, and still is in a compressed state. Therefore, the force of the spring 107 acts upon the cylinder of the drug cartridge 200 via the slide member 108, and the cylinder 201 of the drug cartridge 200 is forced toward the needle attachment portion 102. This force will thereafter continue until the piston 109 retracts and the tip 109a comes apart from the gasket 202. On the other hand, the gasket 202 remains in contact with the tip 109a of the piston 109 until the piston retracts.

With this structure, while the tip 109a of the piston 109 is in contact with the gasket, the cylinder 201 is also held by the force of the spring 107, and the drug cartridge 200 in the cartridge adapter 101 remains in a state in which the drug cartridge 200 is held so as not to move as a whole. As a result, when the injection needle 210 is attached to the drug injection device 11 in this state, even if a needle puncture resistance occurs as a rear needle 211a of the injection needle 210 is inserted through the packing 204, the resistance acts as a resistance against the drug cartridge 200 as a whole and does not change the internal pressure of the cylinder 201. Thus, even if the rear needle 211a is inserted through the packing 204 of the drug cartridge 200, the drug held therein is prevented from being discharged through the needle 211. As a result, the drug in the drug cartridge 200 is prevented from being decreased by the attachment of the injection needle, thereby enhancing the precision with which the amount of drug in the drug cartridge 200 in the drug injection device 11 is controlled.

As shown in FIG. 6(c), when the tip 109a of the piston 109 moves to position P3 so that the slide member 108 comes into contact with the cylinder 201, a protruding portion 108d provided on the slide member 108 fits into a depressed portion 103d provided in the lid 103b of the cartridge holder 103. As a result, the lid 103b is locked, preventing the lid 103b from pivoting. Thus, it is possible to prevent the operator from inadvertently opening the lid 103b and replacing the drug cartridge 200 being used with a drug cartridge 200 of a different type. It is also possible to prevent the operator from opening the lid 103b with the piston 109 inserted in the drug cartridge 200, and forcibly removing the drug cartridge 200, thereby damaging the cartridge adapter 101 or the drug cartridge 200.

From the state in which the piston 109 is located at P3, the piston 109 is inserted into the cylinder 201 by an amount that corresponds to the dose of a single shot, thereby injecting the drug held in the cylinder 201. After the drug of a single shot is discharged, the piston 109 remains its position, and the cartridge holder 103 can be removed from the drug injection device 11 in such a state. As described above, the lid 103b of the cartridge adapter 101 cannot be opened by a normal operation. Since the piston 109 is protected by the piston guide portion 104, the piston 109 will not move during normal use even after the cartridge adapter 101 is removed. Thus, it is possible to safely and stably store the removed cartridge adapter 101. Since there is no need to retract the piston 109 at the time of removal, the cartridge adapter 101 can be removed within a shorter amount of time after the administration of the drug.

When the cartridge adapter 101 is loaded in the drug injection device 11 again, the piston 109 is at such a position that the drug can be administered immediately. Therefore, when the cartridge adapter 101 is re-loaded, there is no need to move the piston to such a position that the drug can be administered, and it is possible to give an injection within a shorter amount of time after turning on the drug injection device 11. Therefore, even when an injection is given by using the drug injection device 11 a plurality of times a day while switching between a plurality of cartridge adapters 101, it takes a short amount of time to load or remove the cartridge adapters 101, and it is possible to shorten the amount of time required for each shot of injection, thus realizing an operability imposing less burden on the operator. Since the amount of movement of the piston 109 is small, it is possible to reduce the capacity of the battery provided in the drug injection device 11, and it is possible to realize a small drug injection device 11 having a good portability.

FIG. 6(d) shows a state in which the gasket 202 is pushed farthest into the cylinder 201 as a result of administering the drug a plurality of times. In this state, the distal end of the tip 109a of the piston 109 is at position P2. Depending on the shape of the cylinder 201, etc., there may remain some drug in the cylinder 201 that cannot be discharged even if the gasket 202 is moved all the way through the movable range.

When the drug cartridge 200 being used is replaced with a new drug cartridge after the drug available has all been injected, the drug injection device 11 with the drug cartridge 200 loaded therein drives the piston 109 so that the piston 109 is retracted to the state of FIG. 6(b), i.e., position P1.

As will be described below in detail, when the drug in the drug cartridge 200 is past its expiration date or when the amount of the drug remaining in the drug cartridge 200 is less than the dose of a single shot, the drug cartridge 200 may be replaced even if the piston 109 has not reached position P2. Also in this case, the drug cartridge 200 can be removed from the cartridge adapter 101 by retracting the piston 109 to position P1 shown in FIG. 6(b).

Figure 7:
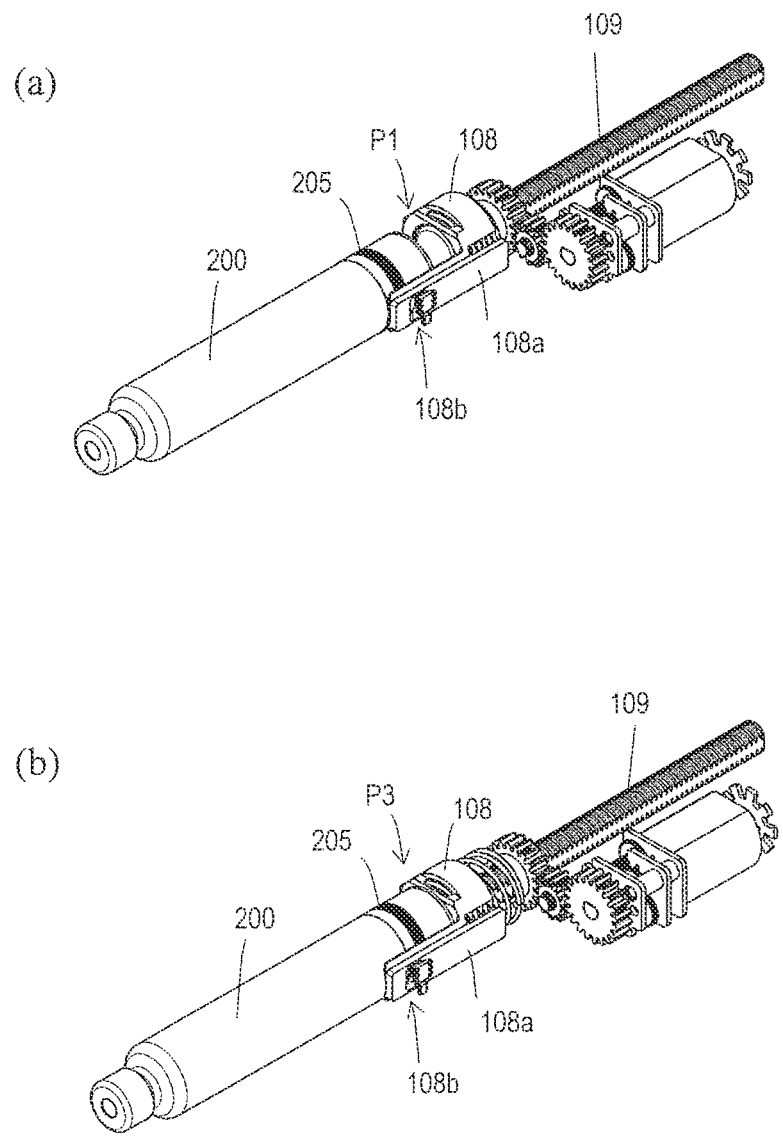
FIGS. 7(a) and 7(b) are perspective views showing the movement of a slide member 108 while a piston 109 moves from position P1 to position P3.

FIGS. 7(a) and 7(b) are perspective views showing the movement of the slide member 108 while the piston 109 moves from position P1 to position P3. The slide member 108 has the shade portion 108a, and the shade portion 108a is provided with the slit 108b. Band-shaped second identification information is provided on the side surface of the cylinder 201 of the drug cartridge 200. As described above, as the piston 109 moves from position P1, the slit 108b provided in the shade portion 108a of the slide member scans the second identification information 205. Using a light emitting element and a light detecting element provided on the side of the drug injection device 11 to detect the light reflecting off the second identification information 205 through the slit 108b, it is possible to detect the second identification information 205. The details will be described below.

[Structure of Drug Injection Device 11]

Figure 9:
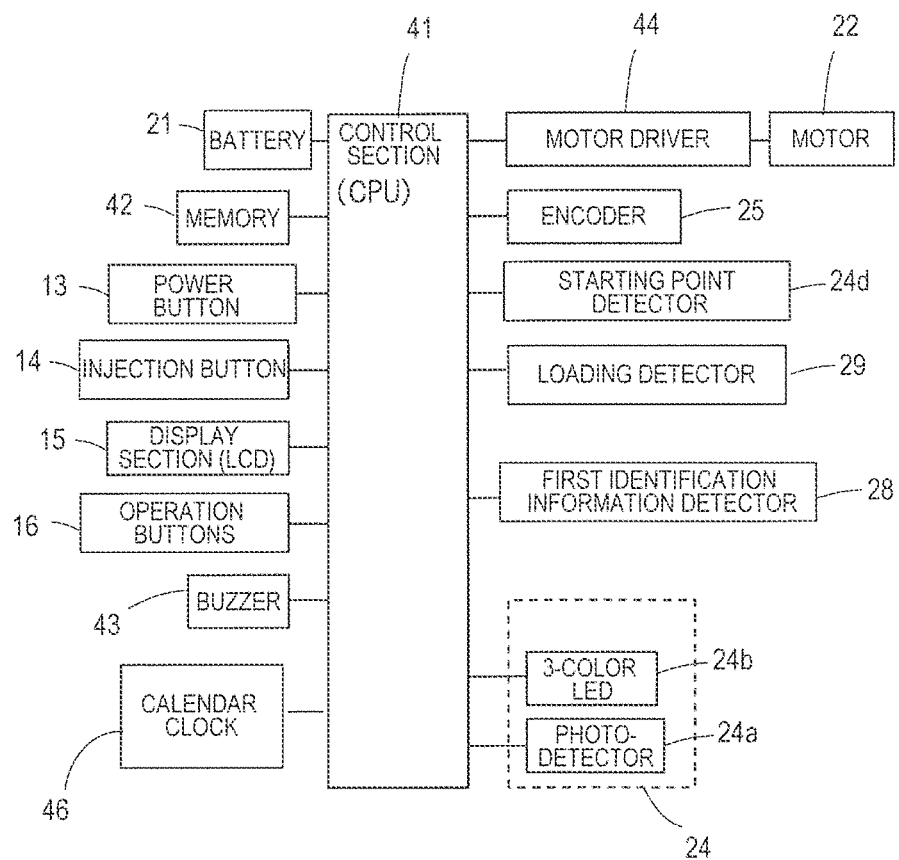
FIG. 9 shows an example of a block diagram of the drug injection device 11.

FIGS. 8(a) and 8(b) are perspective views showing the structure of the drug injection device 11 where the casing 12 is divided in the horizontal direction and the upper half of the casing 12 is removed. FIG. 9 shows an example of a block diagram of the drug injection device 11. The drug injection device 11 includes a battery 21, a driver 32, a second identification information detector 24, a rotary encoder 25, an starting point detector 24d, a loading detector 29, a first identification information detector 28 and a control substrate 31, which are provided in the casing 12.

The battery 21 supplies electric power to the driver 32, the control substrate 31, etc. The battery 21 may be a primary battery or may be a secondary battery. When a secondary battery is used, the drug injection device 11 further includes a circuit for charging the secondary battery, such as a charging circuit.

The driver 32 generates a driving force to rotate the piston gear 105 of the cartridge adapter. The driver 32 includes a motor 22, a transmission 23 and a drive gear 35, for example. The motor 22 may be any of various small motors. The transmission 23 decreases the rotation speed of the motor 22 and transmits the torque to the drive gear 35. It is preferred that the motor 22 or the transmission 23 is provided with the rotary encoder 25. The rotary encoder 25 converts the number of revolutions of one gear of the motor 22 or the transmission 23 into a pulse signal, and outputs the pulse signal. When the motor 22 is a brushless motor, the number of revolutions of the motor may be detected based on the Hall element provided in the brushless motor.

The second identification information detector 24 detects the second identification information 205 located on the outer surface of the drug cartridge 200. The details will be described below. The control substrate 31 includes a controller (an arithmetic circuit, a CPU) 41, a memory 42, a calendar clock 46 and a motor driver 44. An arithmetic circuit 41 executes a computer program read out from the memory 42, and sends instructions to other circuits and components in accordance with the procedure of the computer program. The components having received instructions operate as described above in the present specification, thereby realizing various functions. The procedure of the computer program is shown in flow charts of accompanying drawings to be described below.

The memory 42 may be volatile or may be non-volatile. The memory 42 is preferably a non-volatile RAM. The memory 42 is an example of a non-transitory computer-readable recording medium. An injection schedule for drugs suitable for use with the drug injection system 100 is pre-stored in the memory 42. The injection schedule includes data relating to types and doses of drugs to be injected, timing of injection thereof, etc., for a predetermined period of time, e.g., one day or one week. The injection schedule is input by the patient, the doctor, the technician, etc., according to prescriptions for administering the drugs, for example.

The calendar clock 46 has the clock and calendar function, and provides the date and time information, which serves as the reference of time axis for the injection schedule. Based on the control signal output from the arithmetic circuit 41, the motor driver 44 generates, from the battery 21, electric power for driving the motor 22.

Moreover, as described above with reference to FIG. 1, the arithmetic circuit 41 accepts inputs from the power button 13, the injection button 14 and the operation button 16. The arithmetic circuit 41 outputs various information to the display 15, causing the display 15 to display information. Moreover, the arithmetic circuit 41 receives detection signals from the starting point detector 24d, the loading detector 29 and the first identification information detector 28.

In the drug injection device 11, the position of the piston 109 of the cartridge adapter 101 is determined based on information relating to the rotation of the motor 22, such as the pulse count obtained from the rotary encoder 25. When a plurality of cartridge adapters 101 are switched from one to another, the position of the piston 109 is determined and stored in the memory 42 for each cartridge adapter 101. Specifically, the position of the piston 109 is determined from the number of revolutions of the motor 22. The amount of movement of the piston 109 for injecting a predetermined drug is determined, and the number of revolutions of the motor 22 needed therefor is determined. The position of the piston 109 and the number of revolutions of the motor 22 are determined based on the starting point (the position and the timing of the piston 109) determined by the detection signal of the starting point detector 24d.

As shown in FIGS. 8(a) and 8(b), the casing 12 includes an adapter space 12b in which the majority of the cartridge adapter 101 is accommodated, and the opening 12a that communicates with the adapter space 12b. The flap 20 is provided inside the casing 12 in the vicinity of the opening 12a, and is forced by a force member 33 always in such a direction that the flap 20 is closed, as shown in FIG. 8(a). The force member 33 is an extension spring, for example. While FIG. 8 shows the flap 20 that pivots about a rotation axis, the flap 20 may slide to open/close the opening 12a. The flap 20 may be a double-leaf flap, divided in two parts, for example.

An engagement member 30 and an anti-slip member 26 are provided in the vicinity of the adapter space 12b in the casing 12. The engagement member 30 is forced by a force member 27. The engagement member 30 is provided on the casing 12 and mechanically attached to the lock release lever 18. The engagement member 30 is a hook in the example shown in FIG. 8. The force member 27 is a leaf spring. These structures are used to lock against the removal of the cartridge adapter 101 and to prevent the cartridge adapter 101 from slipping off inadvertently.

FIG. 8(c) is a perspective view showing the structure of the drug injection device 11 that is located on the opposite side of the divided casing 12. As shown in FIG. 8(c), the loading detector 29 and the first identification information detector 28 are provided in a farthest portion of the adapter space 12b.

Figure 10:
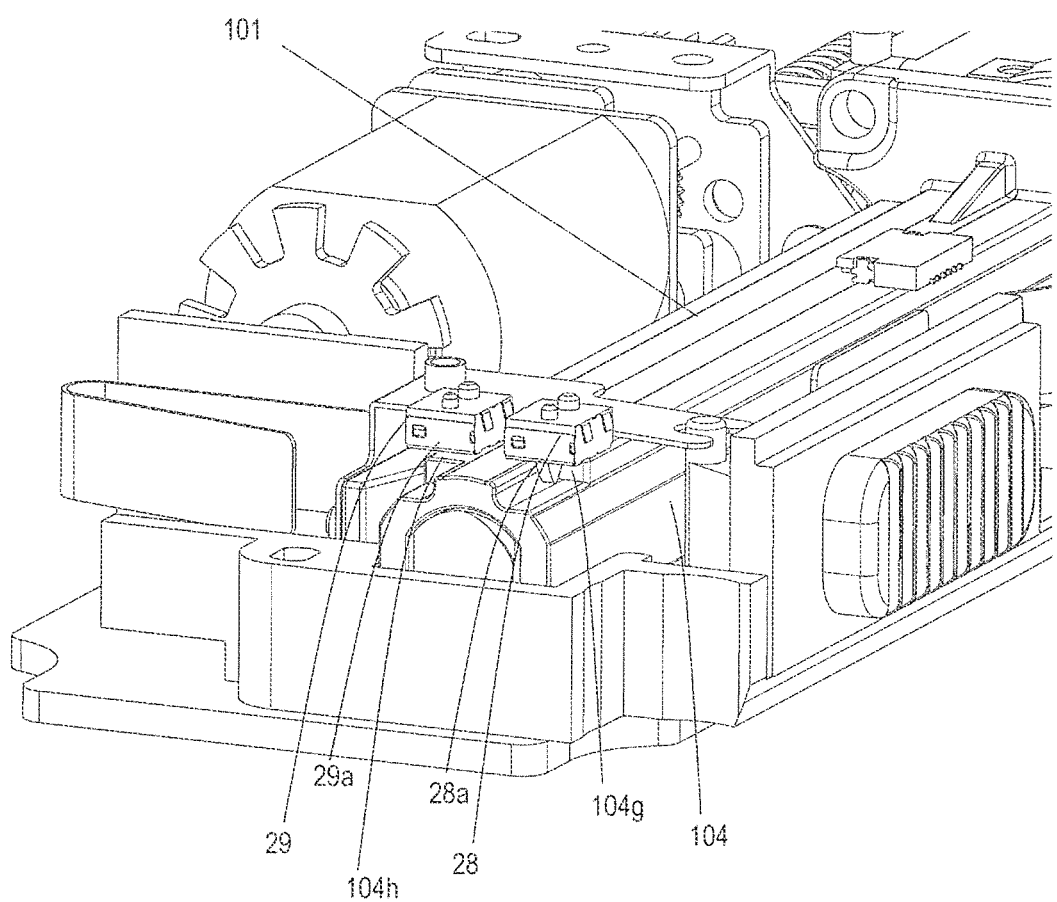
FIG. 10 is a perspective view showing a distal end portion of the cartridge adapter 101 inserted in the casing 12 on an enlarged scale.

FIG. 10 is a perspective view showing a distal end portion of the cartridge adapter 101 inserted in the casing 12 on an enlarged scale. As shown in FIG. 10, the first identification information 104g and the loading information 104h are provided at the distal end of the piston guide portion 104. As described above, the first identification information 104g and the loading information 104h are each a depressed portion or a protruding portion provided on the outer shape of the cartridge adapter 101. For example, the first identification information detector 28 and the loading detector 29 are microswitches having a minute button 28a and a minute button 29a, respectively, and are located in regions corresponding to the first identification information 104g and the loading information 104h, respectively. In FIG. 10, the first identification information 104g is a depressed portion, and the button 28a is not pressed, thereby not causing the first identification information detector 28 to output a detection signal. The loading information 104h is a protruding portion, and the button 29a is pressed, thereby causing the loading detector 29 to output a detection signal.

Thus, the drug injection device 11 can detect loading of the cartridge adapter 101. It is also possible to identify between types of cartridge adapters 101 that accommodate therein different drug cartridges.

Where the first identification information 104g is formed by a depressed portion or a protruding portion provided on the outer shape of the cartridge adapter 101, if there is one first identification information 104g, it is possible to identify between two types of cartridge adapters 101 per first identification information 104g. Accordingly, if there are two pieces of the first identification information 104g, it is possible to identify between four types of cartridge adapters 101. The number of pieces of the first identification information 104g may be determined as needed, and the position at which the first identification information 104g is provided is not limited to the example shown in FIG. 10.

When the loading information 104h and the first identification information 104g are conductors, two terminals located so as to be in contact with the conductors may be used as the detector, for example. When the loading information 104h and the first identification information 104g are magnetic forces, a magnetic sensor, or the like, may be used as the detector. Moreover, when the loading information 104h and the first identification information 104g are optical properties, a light emitting element and a light sensor for detecting light emitted from the light emitting element can be used as the detector.

[Loading and Removing Cartridge Adapter 101 into and from Drug Injection Device 11]

Next, referring to FIG. 11 to FIG. 14, loading and removal of the cartridge adapter 101 to and from the drug injection device 11, and the lock mechanism and the anti-slip mechanism of the drug injection device 11 for locking the cartridge adapter 101 will be described. FIGS. 11(a) to 11(d) show the structure of the drug injection device 11 during the process of removing the cartridge adapter 101 which has been loaded in the drug injection device 11.

As shown in FIG. 11(a), the engagement member 30 is in engagement with the depressed portion 104q provided on the cartridge adapter 101, with the cartridge adapter 101 loaded. The engagement member 30 is mechanically connected to the lock release lever 18. These members together form the lock mechanism. FIG. 12(a) is a perspective view showing the lock mechanism on an enlarged scale.

The anti-slip member 26 is in engagement with the depressed portion 104r of the cartridge adapter 101. These members together form the anti-slip mechanism. FIG. 13(a) is a perspective view showing the anti-slip mechanism on an enlarged scale. These two mechanisms are arranged so as to sandwich the piston guide portion 104 of the cartridge adapter 101 therebetween. Therefore, in this state, even when one attempts to pull out the cartridge adapter 101 in the direction of the arrow shown in FIG. 11(a), it is not possible to move the cartridge adapter 101 because of the engagement of the two mechanisms. Therefore, even when the operator attempts to remove the cartridge adapter 101 in error, for example, it is possible to prevent the cartridge adapter 101 from moving.

As shown in FIG. 11(b), when removing the cartridge adapter 101, the operator slides the lock release lever 18 in the direction indicated by the arrow. Thus, the engagement member connected to the lock release lever 18 pivots about the pivot axis, and the hook of the engagement member comes off the depressed portion 104q of the cartridge adapter 101 as shown in FIG. 12(b). That is, the lock is released. In this state, however, the anti-slip member 26 and the depressed portion 104r remain in engagement with each other, and the cartridge adapter 101 does not slip off only by releasing the lock mechanism. Therefore, it is possible to prevent the cartridge adapter 101 from slipping off inadvertently by virtue of gravity, etc., when the operator merely releases the lock mechanism in order to remove the cartridge adapter 101.

Figure 11:
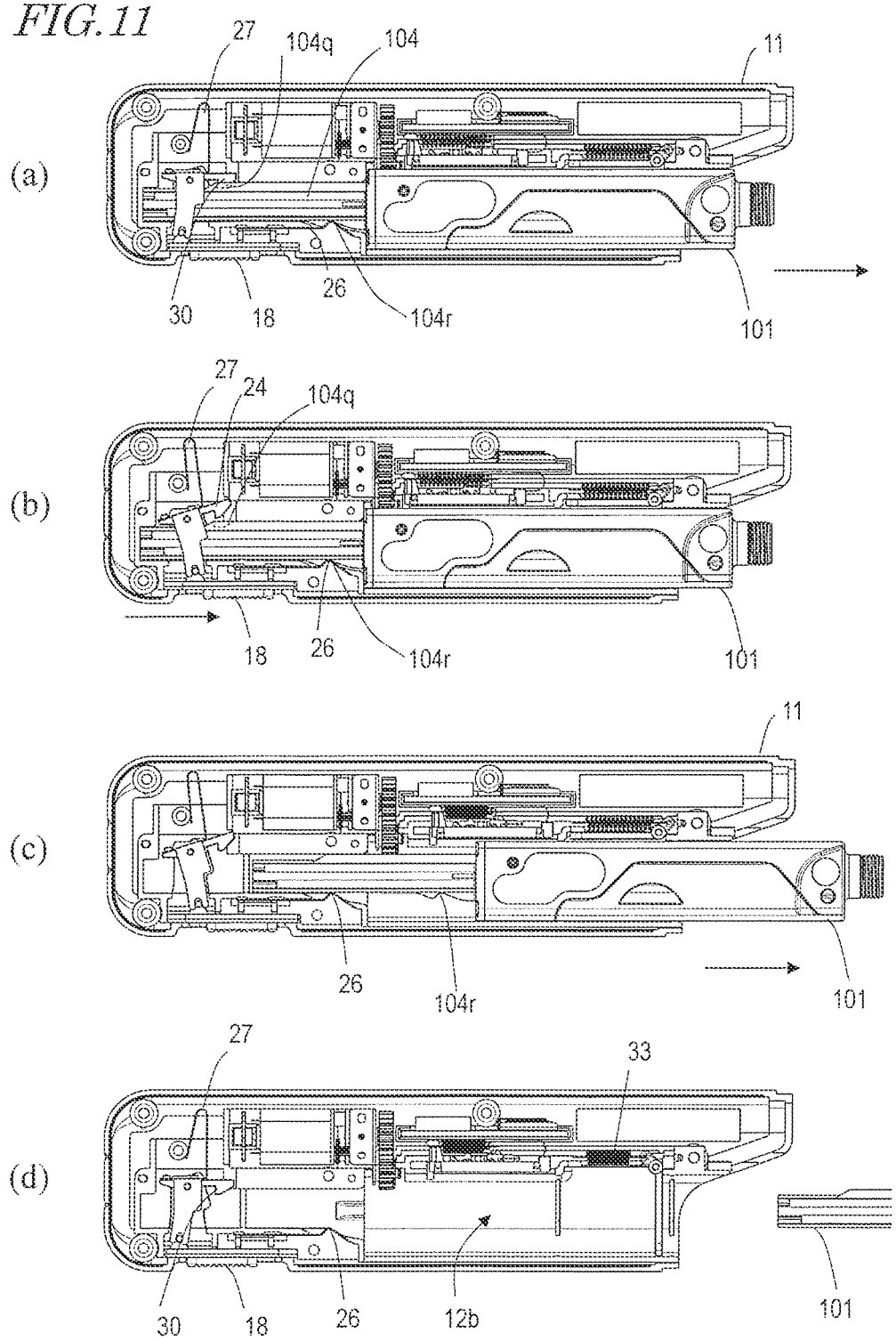
FIGS. 11(a) to 11(d) show the structure of the drug injection device 11 during the process of removing the cartridge adapter 101 which has been loaded in the drug injection device 11.

In the configuration shown in FIG. 11, the engagement member 30 is forced by the force member 27. Therefore, if the lock release lever 18 is slid in the direction of the arrow to release the lock and then the finger is moved away from the lock release lever 18, the hook of the engagement member 30 is again inserted into the depressed portion 104q by virtue of the force applied by the force member 27. The lock release lever 18 also moves in the direction opposite to the arrow. Thus, it returns to the locked state.

As shown in FIG. 11(c), when the cartridge adapter 101 is pulled in the direction of the arrow with the lock release lever 18 being in the slid position, the anti-slip member 26 moves over the wall of the depressed portion 104r of the cartridge adapter 101, thereby releasing the engagement of the anti-slip mechanism, as shown in FIG. 13(b). Moreover, the hook of the engagement member 30 of the lock mechanism comes off the depressed portion 104q and moves out of the depressed portion 104q. In this state, when the cartridge adapter 101 is further pulled in the direction of the arrow, the cartridge adapter 101 can be removed completely as shown in FIG. 11(d). When the cartridge adapter 101 is removed so that the entirety thereof is located completely outside the adapter space 12b, the opening 12a is automatically shut by the flap 20 by virtue of the force applied by the force member 33. Therefore, the operator will not leave the flap 20 open, and the operator does not need to worry about opening/closing the flap 20.

When a cartridge adapter is loaded in the drug injection device 11, the distal end of the piston guide portion 104 of the cartridge adapter 101 is pressed against the flap 20 of the opening 12a, and the cartridge adapter 101 is inserted into the inside of the casing 12. In this case, the insertion of the cartridge adapter 101 is completed as shown in FIG. 11(a) by inserting the cartridge adapter 101 against the forces applied by the anti-slip member 26 and the force member 27. At this point, the engagement member 30 is in engagement with the depressed portion 104q of the cartridge adapter 101, and the anti-slip member 26 is in engagement with the depressed portion 104r of the cartridge adapter 101.

FIGS. 14(a) and 14(b) are perspective views showing, on an enlarged scale, the vicinity of the piston gear 105 of the cartridge adapter 101 and the drive gear 35 of the drug injection device 11. When inserting the cartridge adapter 101 into the drug injection device 11, the piston gear 105 of the cartridge adapter 101 needs to be meshed with the drive gear 35 of the drug injection device 11. However, depending on the rotation angles of the piston gear 105 and the drive gear 35 being at a halt, the teeth of the two gears may come into contact with each other, preventing the insertion of the cartridge adapter 101 or resulting in an inadequate insertion.

In order to avoid such problems, it is preferred that a taper 35a is provided on the end surface (on the opening 12a side) of each tooth of the drive gear 35 as shown in FIG. 14(a). Moreover, it is preferred that a taper 105fa is provided on the end surface (on the piston guide portion 104 side) of each tooth of the piston gear 105 as shown in FIG. 14(b). Thus, even if the teeth of the piston gear 105 come into contact with the teeth of the drive gear 35 during the insertion of the cartridge adapter 101, the taper 35a of the drive gear 35 comes into contact with the taper 105fa of the piston gear 105, thereby allowing the force of insertion of the cartridge adapter 101 to serve to slightly move at least one of the gears. Therefore, the teeth of one gear are inserted into the grooves of the other gear, thereby properly meshing the piston gear 105 of the cartridge adapter 101 with the drive gear 35 of the drug injection device 11. As a result, when loading the cartridge adapter 101 in the drug injection device 11, the cartridge adapter 101 can be inserted smoothly within a short amount of time without the operator having to pay attention to the rotation angle positions of these gears. That is, it is possible to reduce the burden of the operator when loading the cartridge adapter 101.

Thus, according to the present embodiment, a high level of safety and a high level of operability are provided for loading and removing the cartridge adapter 101 to and from the drug injection device 11. Moreover, since replacing the cartridge adapter 101 requires a short amount of time and is easy, there is little burden on the operator even if the number of times the cartridge adapter 101 is replaced is increased.

[Structure and Operation of Second Identification Information Detector 24]

Figure 15:
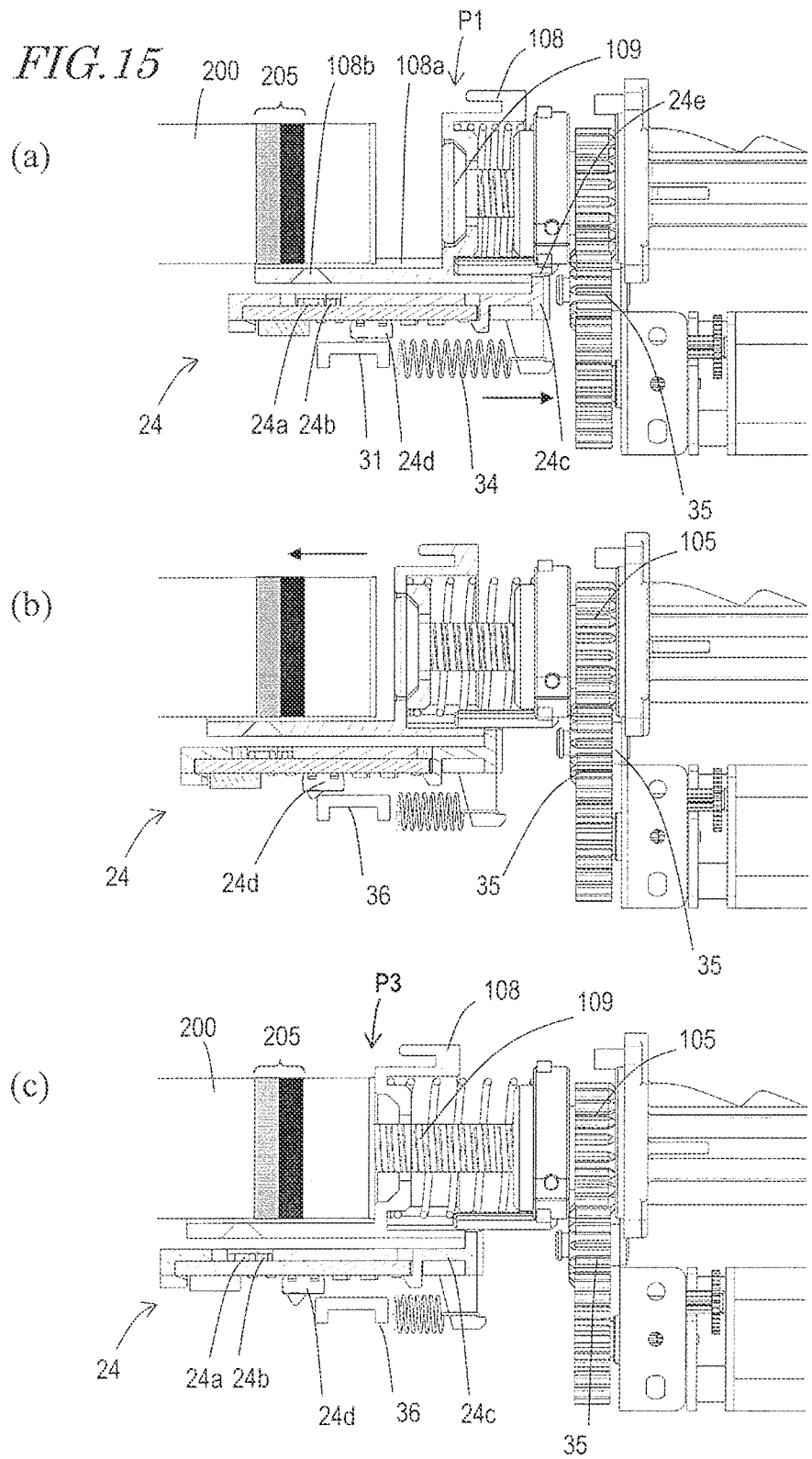
FIGS. 15(a), 15(b) and 15(c) are diagrams showing, on an enlarged scale, the vicinity of a second identification information detector 24 when a tip 109a of a piston 109 of the cartridge adapter 101 is at position P1 (the most retracted position), between positions P1 and P3, and at position P3, respectively.
Figure 16:
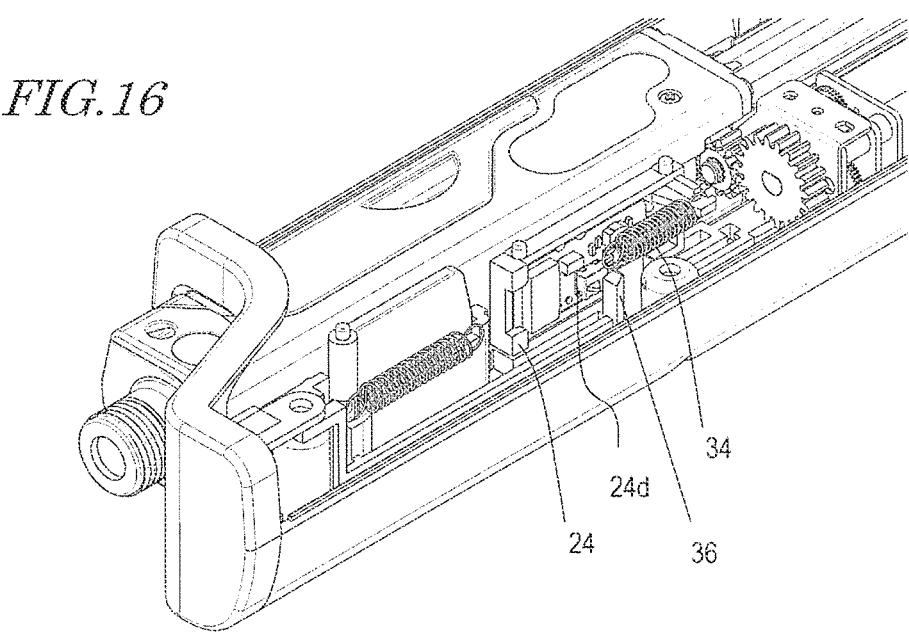
FIG. 16 is a partially enlarged perspective view showing the contact between an starting point detector 24d and a contact portion 36.
Figure 17:
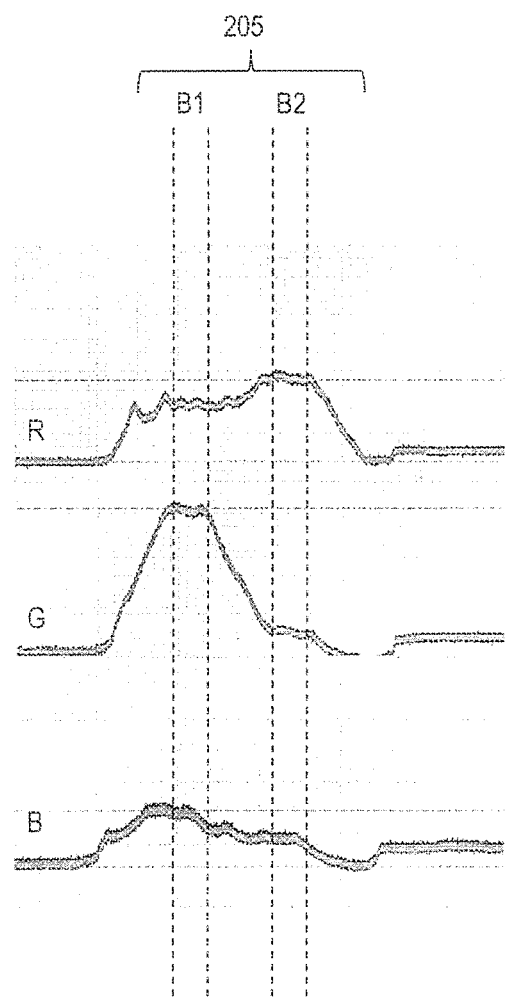
FIG. 17 shows an example of a detection result of the second identification information detector 24.

Referring to FIG. 15 to FIG. 17, the structure and the operation of the second identification information detector 24 will be described in detail. As described above, in the present embodiment, the type of the cartridge adapter 101 and the type of the drug cartridge 200 to be accommodated therein have a one-to-one correspondence, and each cartridge adapter 101 has a predetermined type of a drug cartridge 200 to be inserted into the cartridge adapter 101. However, it is possible to accommodate an incompatible drug cartridge 200. Therefore, when a drug cartridge 200 of the cartridge adapter 101 is replaced with another drug cartridge 200, the drug injection device 11 detects the second identification information 205 provided on the drug cartridge 200, i.e., a color unique to the drug, thereby identifying the type of the drug cartridge 200.

FIGS. 15(a), 15(b) and 15(c) are diagrams showing, on an enlarged scale, the vicinity of the second identification information detector 24 when the tip 109a of the piston 109 of the cartridge adapter 101 is at position P1 (the most retracted position), between position P1 and position P3, and at position P3, respectively.

As shown in FIG. 15(a), the second identification information detector 24 includes a base 24c, and a photodetector 24a, a light emitting element 24b and the starting point detector 24d provided on the base 24c. The base 24c is supported, on the casing 12, slidably in the longitudinal direction, which is the direction in which the piston 109 moves, and is forced by a force member 34 toward the opening 12a. In the present embodiment, the light emitting element 24b emits red, blue and green light beams, and the photodetector 24a can detect the intensity of light in the white light range. The light emitting element 24b is an LED capable of separately emitting RGB light beams, for example, and the photodetector 24a is a photodiode, or the like.

When the cartridge adapter 101 is inserted into the drug injection device 11, one end of the shade portion 108a of the slide member 108 of the cartridge adapter 101 comes into contact with a projection 24e of the base 24c, thereby moving the base 24c in the direction of the arrow of FIG. 15(a). In this state, the slit 108b of the shade portion 108a is aligned with the position of the photodetector 24a and the light emitting element 24b. The light emitting element 24b outputs light onto the side surface of the cylinder 201 of the drug cartridge 200 of the cartridge adapter 101 through the slit 108b, and the light reflecting off the side surface is detected by the photodetector 24a through the slit 108b.

When replacing a drug cartridge, the piston 109 is at position P1 and is most retracted. Therefore, even when the cartridge adapter 101 with the replaced drug cartridge 200 is accommodated therein is loaded, the piston 109 is at position P1. At this point, the tip 109a of the piston 109 is not in contact with the gasket 202, and the slide member 108 is also away from the cylinder 201. The second identification information 205, which is a color region, is provided on the outer surface of the cylinder 201. The slit 108b of the shade portion 108a is located closer to the end portion of the drug cartridge 200 than the second identification information 205. An starting point detector 204d is in contact with the contact portion 36 provided on the casing 12.

As shown in FIG. 15(b), the piston gear 105 is rotated by the rotation of the drive gear 35, thereby moving the piston 109 in the direction of the arrow. Accordingly, the slide member 108 forced by the spring 107 also moves in the arrow direction. As a result, the base 24c of the second identification information detector 24 forced by the force member 34 also moves in the direction of the arrow. Since the slide member 108 moves in the arrow direction together with the base 24c, the photodetector 24a and the light emitting element 24b scan the outer surface of the cylinder 201 through the slit 108b of the shade portion 108a. As shown in FIG. 16, as the base 24c moves, the contact between the starting point detector 24d and the contact portion 36 is released. Based on the signal from the starting point detector 24d at this point, the number of revolutions of the rotary encoder 25 can be correlated with the position of the piston 109, and it is possible to set the position of the piston 109 to the starting point and the number of revolutions of the motor to the starting point (zero), for example. The contact between the starting point detector 24d and the contact portion 36 may be released at any point between position P1 and position P3. That is, there is no limitation as long as the starting point is determined before the piston reaches position P3 and an injection of the drug is ready to be given.

When the piston 109 is further moved as shown in FIG. 15(c), the tip 109a comes into contact with the gasket 202, the slide member 108 comes into contact with the end portion of the cylinder 201, and the piston 109 reaches position P3. In this state, the slit 108b of the shade portion 108a is located past the second identification information 205 and on the side of a distal end 201a of the cylinder 201. Thus, the scan of the second identification information 205 by the photodetector 24a and the light emitting element 24b is complete. The rotation of the motor is stopped, thereby stopping the movement of the piston 109. Thus, the movement of the piston 109 to a position where the drug can be inject is complete. The piston 109 can be stopped at position P3 by, for example, moving the piston 109 by a predetermined distance by counting the number of revolutions of the motor from the starting point detection described above.

In order to detect the second identification information 205 by the photodetector 24a and the light emitting element 24b, red, blue and green light beams are emitted to obtain the detection intensity of the photodetector 24a and the position (time) of detection for each color, for example. The piston 109 is moved by a minute amount Δx, for example, and red, blue and green light beams are emitted while the movement of the piston has been stopped, to obtain the light intensity for each light beam emitted. This is repeated between position P1 and position P3. Alternatively, first, a red light beam is emitted continuously while the piston is moved from position P1 to position P3 to obtain the light intensity for each light beam emitted. When the piston reaches position P3, the position of the piston is returned to position P1. This may be repeated also for blue and green.

FIG. 17 shows an example of a detection result of the second identification information detector 24. FIG. 17 shows light intensities obtained when light beams of red (R), green (G) and blue (B) are emitted. The horizontal axis represents the position of the slit 108b, and the vertical axis represents the intensity. Over the region of the second identification information 205, the intensity varies for different light beams. This is because the second identification information 205 is provided with colors, and the intensity of reflected light varies for each combination of the light beam used and the colors of the second identification information 205. In the example of FIG. 17, the second identification information 205 includes two band-shaped regions of different colors. At opposite ends of the second identification information 205, there is an influence of non-colored portions, and the detection results include influences from colors other than those of the two bands. There is an influence of two colors in the vicinity of the region where the two color bands are in contact with each other. However, regions denoted as B1 and B2 in FIG. 17 are not influenced as much. Therefore, using the detection results for the three colors over B1 and B2, it is possible to identify colors provided on the second identification information 205.

For example, it is possible to identify a color based only on the magnitude relationship between the red (R), green (G) and blue (B) signal intensities over B1 or B2. Specifically, where the detection intensities of these colors are denoted as SR, SG and SB, it is possible to identify a color based on the magnitude relationship between the intensities of the three signals, e.g., which one of SR>SG>SB, SG>SR>SB, SB>SR>SG, etc., is satisfied. Since colors to be used are predetermined, there is no need to determine the color itself provided on the second identification information 205, but it is possible to identify the color used based on which magnitude relationship is satisfied between the signal intensities.

By using the second identification information detector 24 configured as described above, the second identification information can be identified while the piston 109 is moved to such a position that the drug can be inject after the cartridge adapter 101 is first loaded in the drug injection device 11 after replacing the drug cartridge 200. Therefore, even if the drug cartridge 200 is replaced without taking extra time for identifying the drug cartridge 200, it is possible to use the drug injection device 11 within a short amount of time.

When identifying the color of the second identification information by the second identification information detector 24, the detection is performed through the slit 108b of the shade portion 108a of the slide member 108. Therefore, it is possible to limit light to enter the photodetector 24a, and it is possible to accurately identify the second identification information even under various environments without being influenced by ambient lighting environment, brightness, etc. Therefore, it is possible to accurately control drugs without being influenced by the environment.

[Presentation of Visual Feature]

FIGS. 18(a) and 18(b) show examples of visual features provided on drug cartridges 200 and 200' and cartridge adapters 101 and 101'. As described above, visual features are presented primarily to the operator.

A visual feature is at least one selected from a color, a pattern and a symbol, and may be a combination thereof. For example, as shown in FIG. 18(a), the drug cartridges 200 and 200' may have the visual features 220a and 220b each being a number printed in white against a predetermined background color (a combination of a color and a symbol). In FIG. 18(a), different colors are represented by different shades of gray. With the visual feature 220a and the visual feature 220b differing from each other in terms of the number and the color, the operator can intuitively recognize that the drug cartridge 200' and the drug cartridge 200 are filled with different drugs.

As shown in FIG. 18(b), visual features 120a and 120b provided on the regions 103r2 of the cartridge adapters 101 and 101' use the same numbers, and the same colors, as those of the visual features 220a and 220b. The regions 103r1 are provided with the same visual features 121a and 121b as the visual features 220a and 220b. Thus, the operator can easily understand that the operator should use the drug cartridge 200 with the cartridge adapter 101 and use the drug cartridge 200' with the cartridge adapter 101'.

The visual features 120a and 120b each include a symbol and characters representing the insertion direction, and are not the same as the visual feature 220a and the visual feature 220b. However, with the same number and the same color used, the visual feature 120a and the visual feature 220a are similar to each other, and the operator understands that these features correspond to each other.

By providing such visual features on the drug cartridge 200 and the cartridge adapter 101, it is possible to reduce the possibility that the operator mixes up drugs. By using visual features that can be easily recognized and identified, it is possible to select an appropriate drug cartridge without requiring a long time to make the judgment.

Figure 19:
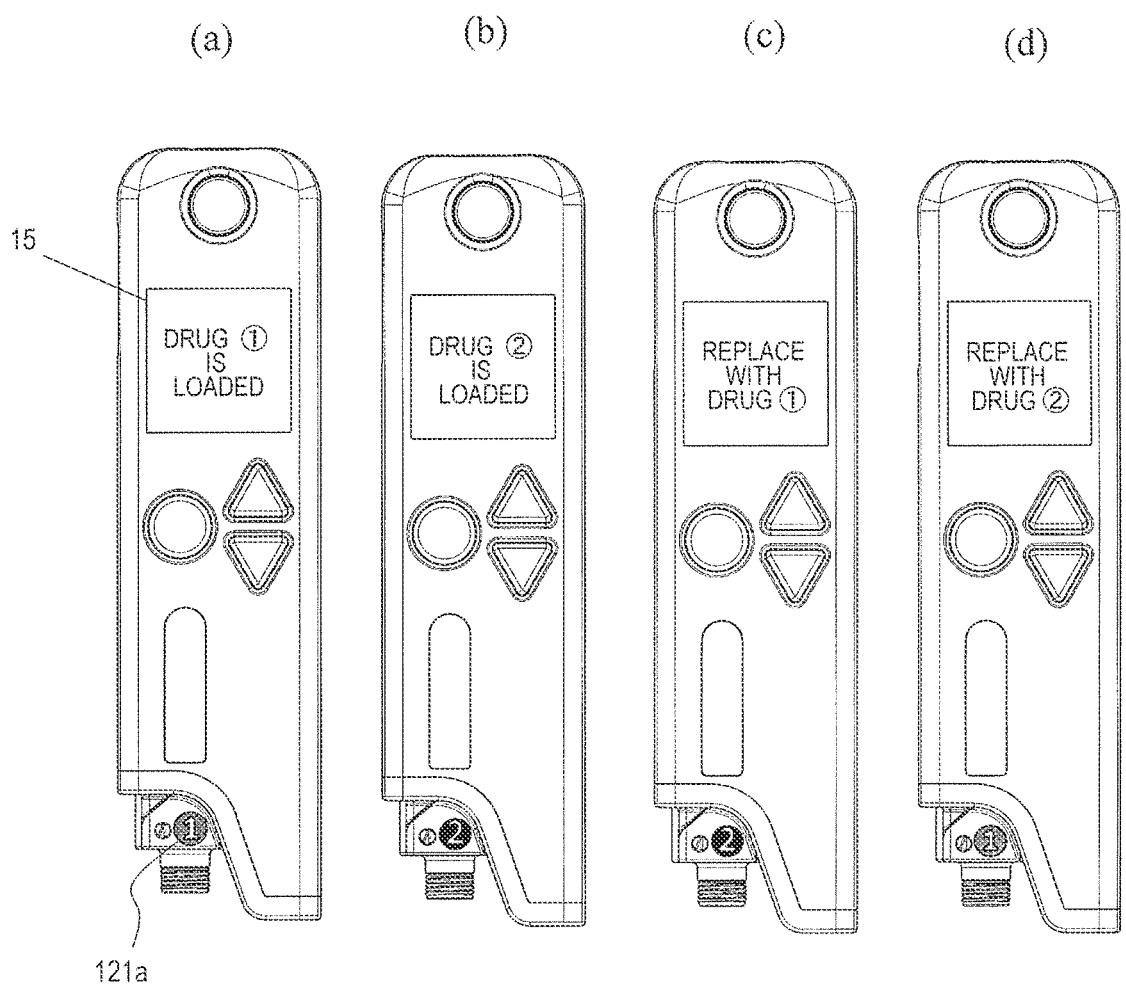
FIGS. 19(a) to 19(d) show examples of visual features displayed on a display.

The visual features described above or similar visual features may be displayed on the display 15 of the drug injection device 11. As shown in FIGS. 19(a) and 19(b), with the cartridge adapter 101 loaded in the drug injection device 11, most of the external appearance of the cartridge adapter 101 is not exposed from the drug injection device 11. Therefore, for example, the drug injection device 11 may display visual features described above based on the result of detecting the first identification information of the cartridge adapter 101. Thus, the operator can check the cartridge adapter 101 that is loaded even in such a state that the cartridge adapter 101 is mostly invisible. As shown in FIGS. 19(a) and 19(b), when the visual feature 121a of the cartridge adapter 101 is exposed, one can confirm that the drug injection device 11 is operating normally by confirming that the visual feature displayed on the display 15 matches the visual feature 121a of the cartridge adapter 101.

As shown in FIGS. 19(c) and 19(d), based on information of the injection schedule stored in the memory 42 and the detection result of the first identification information detector 28, if no cartridge adapter 101 is loaded or if the cartridge adapter 101 of a drug that is not according to the injection schedule is loaded, a visual feature corresponding to the type of the drug that should be loaded or a feature similar to this may be displayed on the display 15.

(Operation of Drug Injection System 100)

Referring to the flow charts shown in FIG. 1 and FIG. 20 to FIG. 26, the operation of the drug injection system 100 including the cartridge adapter 101 and the drug injection device 11 will be described below. Data of the injection schedule is pre-stored in the memory 42 of the drug injection device 11. Moreover, the correct date and time are set in the calendar clock 46. The procedure of the following operation according to the flow charts shown in FIG. 20 to FIG. 26 is stored in the memory 42 in the form of one or more computer program, and the following operation is performed as the arithmetic circuit 41 executes a computer program called from the memory 42 depending on the process. Therefore, while the arithmetic circuit 41 is the main unit for controlling the drug injection device 11, the description below will not particularly refer to the arithmetic circuit 41. To display, as used in the following operation, refers to displaying on the display 15.

Figure 20:
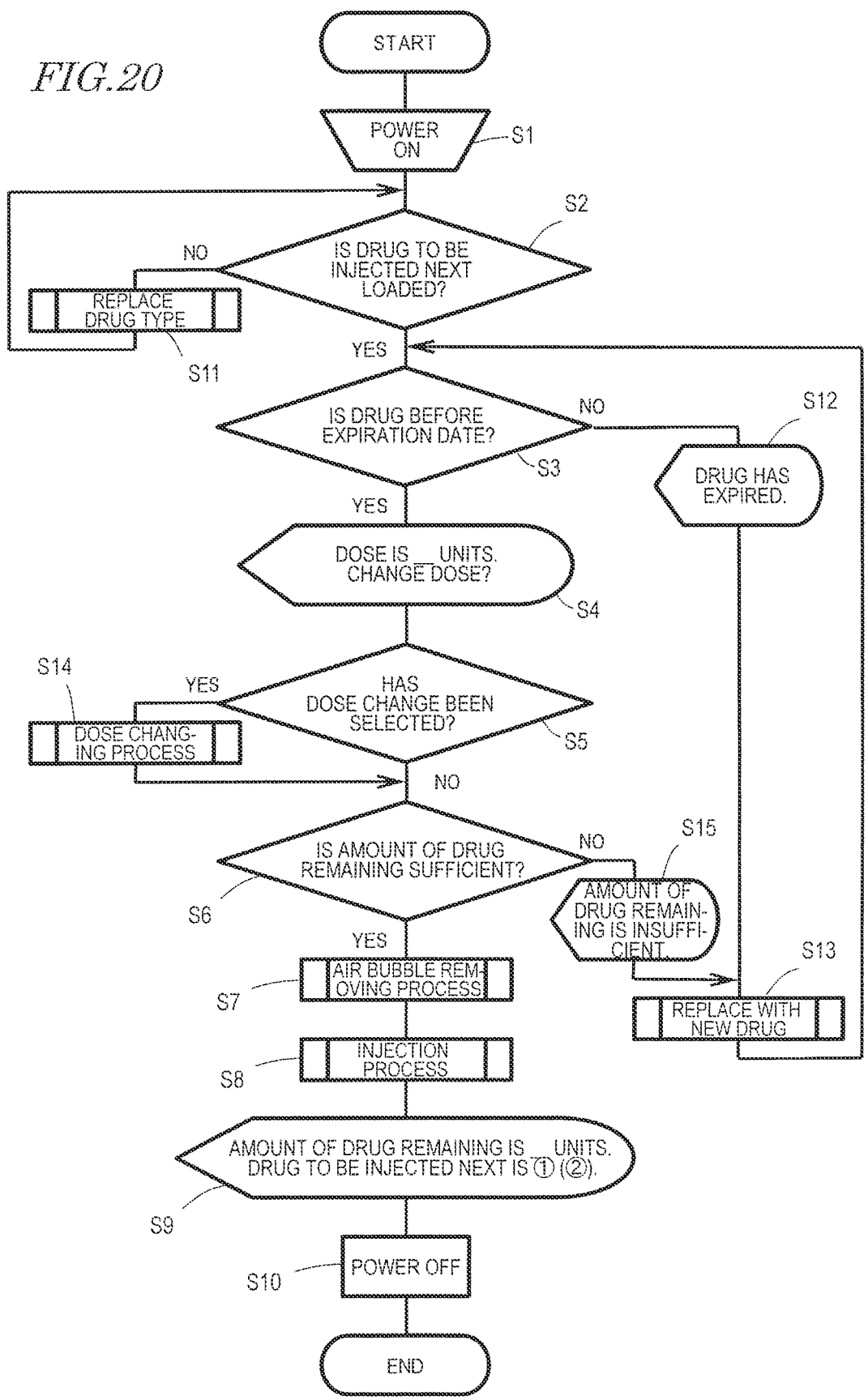
FIG. 20 is a flow chart showing an operation of the drug injection system.

[Main Flow: FIG. 20]

First, the user presses the power button 13 (S1), thereby turning on the drug injection device 11. When the drug injection device 11 is turned on, the process determines whether the cartridge adapter 101 of a drug to be injected next is loaded based on the date and time of the calendar clock 46, the injection schedule, the detection result of the first identification information detector 28 and the detection result of the loading detector 29 (S2). If not, the process performs the drug type replacing flow (S11).

If the cartridge adapter 101 of a drug to be injected next is loaded, the process determines whether the drug of the drug cartridge 200 is before its expiration date. The date on which the cartridge adapter 101 is first loaded in the drug injection device 11 is stored in the memory 42, and the expiration date is determined with reference to the date.

When the drug is past its expiration date, a message is displayed indicating that the drug has expired (S12), and the process performs the flow of replacing with a new drug (S13).

If the drug is before its expiration date, the dose is displayed, and a message is displayed asking the user whether or not to change the dose (S4). When dose change is selected using an operation button 16, the process performs the dose changing process flow (S14). When the dose is not to be changed or after the dose changing process flow (S14), the process determines whether an amount of drug that is greater than or equal to the dose is left in the drug cartridge 200 in the cartridge adapter 101. The amount of drug in the drug cartridge 200 is determined by storing and referring to the dose in the memory 42 each time an injection is performed.

If an amount of drug that is greater than or equal to the dose is not left, a message is displayed indicating that the amount of the drug is insufficient (S15), and the process performs the flow of replacing with a new drug (S13).

When an amount of drug that is greater than or equal to the dose is left, the process performs the air bubble removing process flow (S7) and performs the injection process flow (S8).

After the completion of the injection, a message is displayed indicating the remaining amount of the drug and the next injection schedule (the drug of the next shot and the time as necessary) (S9).

Thereafter, the operator presses the power button 13 to turn off the drug injection device 11. Thus, the main flow ends.

Figure 21:
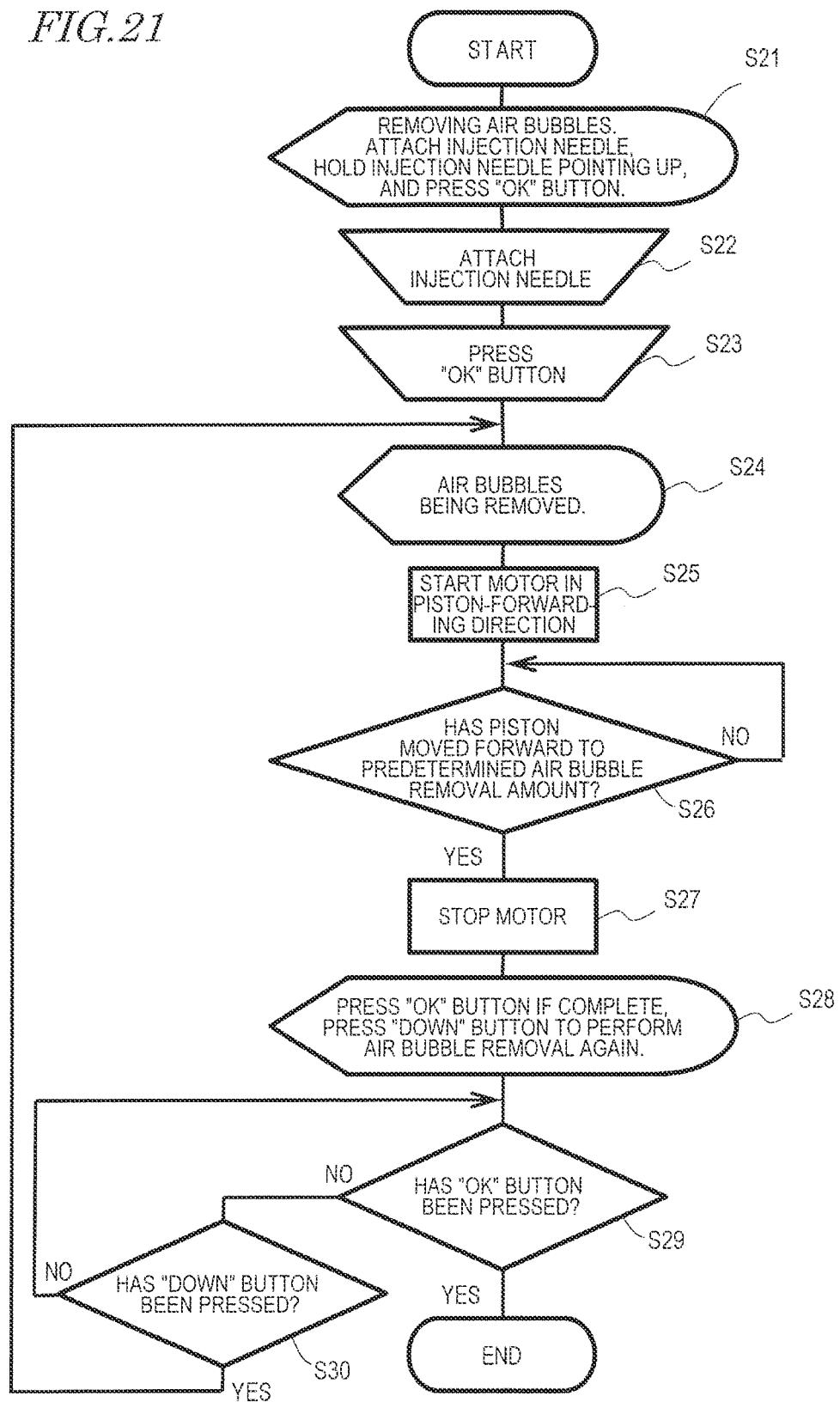
FIG. 21 is a flow chart showing an operation of the drug injection system.

[Air Bubble Removing Process Flow: FIG. 21]

When air bubble removal is needed, first, a message is displayed prompting the user to perform air bubble removal, attach the injection needle and hold the injection needle pointing up (S21).

The operator attaches the injection needle 210 to the needle attachment portion 102 (S22), and presses an operation button 16 (e.g., a button of a circular shape) (S23).

A message is displayed indicating that air bubbles are being removed (S24), and the motor 22 is rotated, thereby rotating the drive gear 35 and the piston gear 105, so as to move the piston 109 forward by a predetermined amount (S25). The piston is moved until a predetermined air bubble removal amount is reached (S26), and the motor 22 is stopped (S27).

A message is displayed prompting the user to determine whether to end the air bubble removal or to further perform air bubble removal (S28). Whether air bubble removal is further needed is generally determined by the operator by checking whether or not liquid has been pushed out of the needle tip.

The process determines whether or not an operation button 16 that is the OK button has been pressed (S29), and if so, ends the air bubble removing process flow. If an operation button 16 (e.g., a button of an inverted triangular shape indicating down) indicating to further perform air bubble removal is pressed, steps S24 to S29 are repeated. Thus, the air bubble removing process flow ends.

Figure 22:
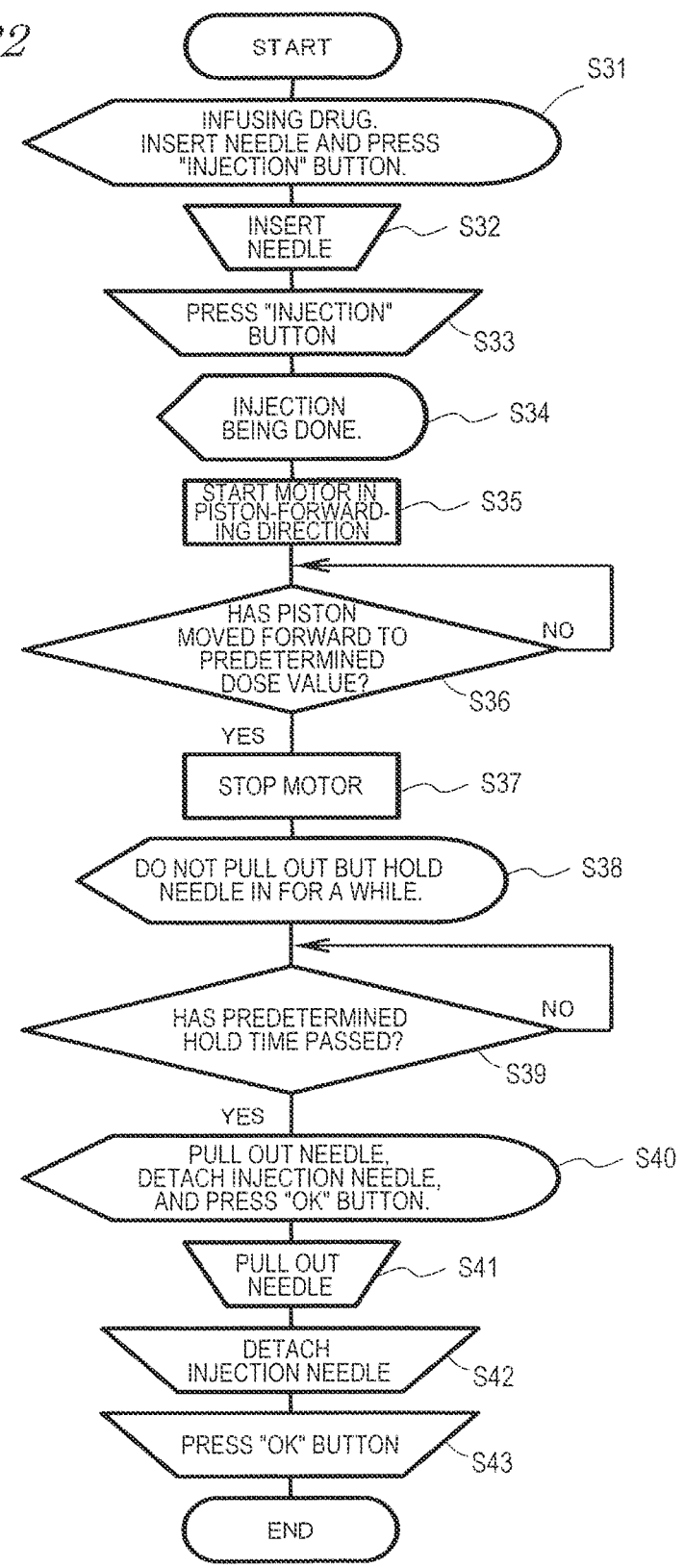
FIG. 22 is a flow chart showing an operation of the drug injection system.

[Injection Process Flow: FIG. 22]

When the injection process is performed, first, a message is displayed indicating that an injection is to be performed, and a message is displayed prompting the user to insert the needle and press the injection button 14 (S31).

When the operator inserts the needle (S32) and presses the injection button 14 (S33), a message is displayed indicating that injection is being done (S34). The motor 22 is rotated, thereby rotating the drive gear 35 and the piston gear 105, so as to move the piston 109 forward by a predetermined amount (S35). The piston is moved until a predetermined dose is reached (S36), and the motor 22 is stopped (S37).

Then, a message is displayed prompting the user not to pull out the needle but to hold the needle in for a while (S38). The drug injection may sometimes continue for a while after the motor 22 is stopped, and this will avoid a situation where the needle is pulled out prematurely, failing to inject a predetermined amount of the drug.

After the passage of a predetermined amount of time (a few seconds to about ten seconds) (S39), a message is displayed prompting the user to pull out the needle, detach the injection needle and press the OK button (S40).

The operator pulls out the needle (S41), detaches the injection needle (S42), and presses the OK button (S43). Thus, the injection process flow ends.

Figure 23:
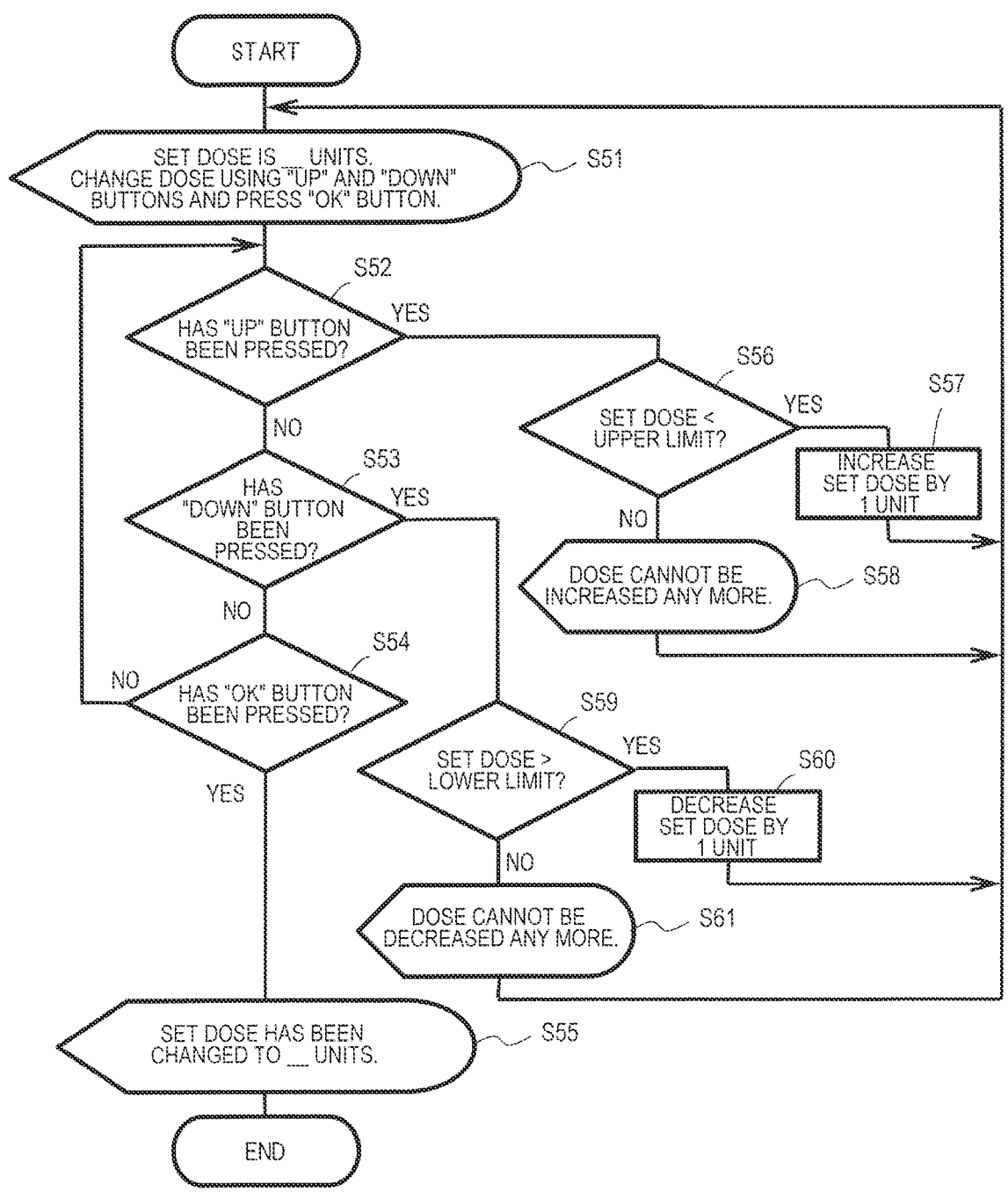
FIG. 23 is a flow chart showing an operation of the drug injection system.

[Dose Changing Process Flow: FIG. 23]

When performing the dose changing process, the dose currently set is displayed, and a message is displayed prompting the user to change the value of the dose using the operation button 16 and press the OK button (S51).

When an operation button 16 that is the up button (a button of a triangular shape) is pressed (S52), the process determines whether or not the changed dose exceeds the predetermined upper limit (S56). If not, the dose is increased by 1 unit (S57), and the process returns to step 51. If the dose exceeds the upper limit, a message is displayed indicating that the dose cannot be increased any more (S58), and the process returns to step 51.

When an operation button 16 that is the down button is pressed (S53), the process determines whether or not the changed dose is below the predetermined lower limit (S59). If it is not below the lower limit, the dose is decreased by 1 unit (S60), and the process returns to step 51. If the dose is below the lower limit, a message is displayed indicating that the dose cannot be decreased any more (S61), and the process returns to step 51.

It is determined whether or not the OK button has been pressed (354). The process returns to step 51 until the OK button is pressed. When the OK button is pressed, a message is displayed indicating that the dose has been changed (S55). Thus, the dose changing process flow ends.

Figure 24:
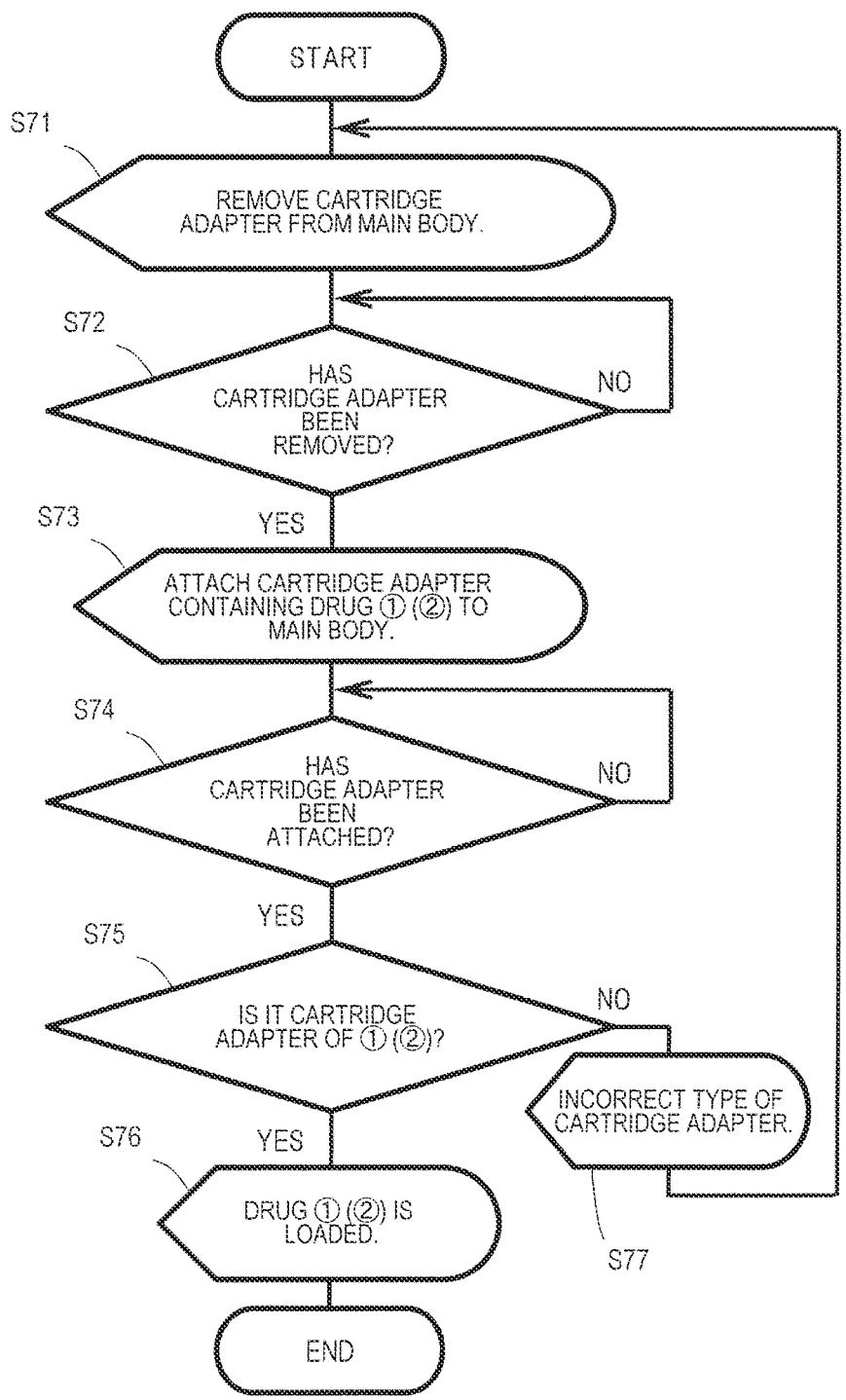
FIG. 24 is a flow chart showing an operation of the drug injection system.

[Drug Type Replacing Flow: FIG. 24]

When switching the drug type, a message is displayed prompting the user to remove the cartridge adapter (S71).

It is determined, based on the signal from the loading detector 29, whether or not the cartridge adapter 101 has been removed (S72).

When the cartridge adapter 101 has been removed, a message is displayed prompting the user to load a cartridge adapter of another drug that should be loaded next (S73).

Based on the signal from the loading detector 29, it is determined whether or not the cartridge adapter 101 has been loaded (S74).

When the cartridge adapter 101 has been loaded, it is determined, based on the signal from the first identification information detector 28, whether or not it is a cartridge adapter 101 of the type that should be loaded (S75).

When it is not a correct cartridge adapter 101, a message is displayed indicating that there is an error (S77), and the process returns to step 71.

When a correct cartridge adapter 101 has been loaded, the type of the cartridge adapter 101 loaded is displayed (S76). Thus, the drug type replacing flow ends.

Figure 25:
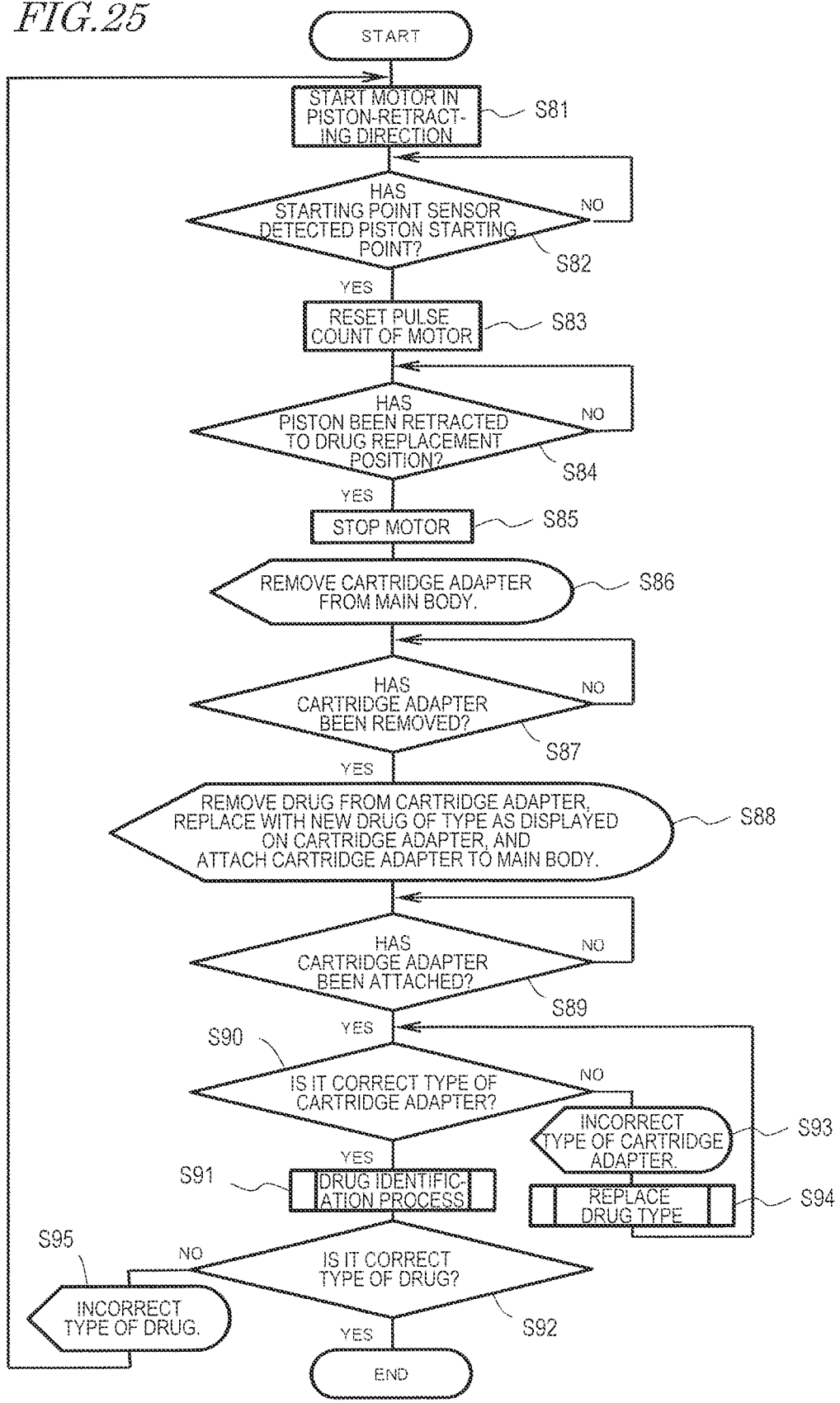
FIG. 25 is a flow chart showing an operation of the drug injection system.

[Flow of Replacing with New Drug: FIG. 25]

When replacing with a new drug, the motor 22 is rotated, thereby rotating the drive gear 35 and the piston gear 105, so as to retract the piston 109 (S81). It is determined whether or not the starting point detector 24d has detected the starting point (S82), and if it has, the process resets the number of revolutions of the motor based on the signal from the rotary encoder 25.

When the piston is retracted to a position for drug replacement (position P1) (S84), the motor 22 is stopped (S85).

A message is displayed prompting the user to remove the cartridge adapter (S86), and it is determined, based on the signal from the loading detector 29, whether or not the cartridge adapter 101 has been removed (S87).

When the cartridge adapter 101 has been removed, a message is displayed prompting the user to remove the used drug cartridge 200 from the cartridge adapter, insert a new drug cartridge of the same type, and load the cartridge adapter 101 (S88).

Based on the signal from the loading detector 29, it is determined whether or not the cartridge adapter 101 has been loaded (S89).

When the cartridge adapter 101 has been loaded, it is determined, based on the signal from the first identification information detector 28, whether or not it is a cartridge adapter 101 of the type that should be loaded (S90).

When it is not a correct cartridge adapter 101, a message is displayed indicating that there is an error (S93), and the process performs the drug type replacing flow (S94). Then, the process returns to step 90.

When a correct cartridge adapter 101 has been loaded, the process performs the drug identification process flow (S91).

When a correct drug cartridge 200 is inserted, the process ends. When an incorrect drug cartridge 200 is inserted, a message is displayed indicating an incorrect drug cartridge (S95), and the process returns to step 81.

Figure 26:
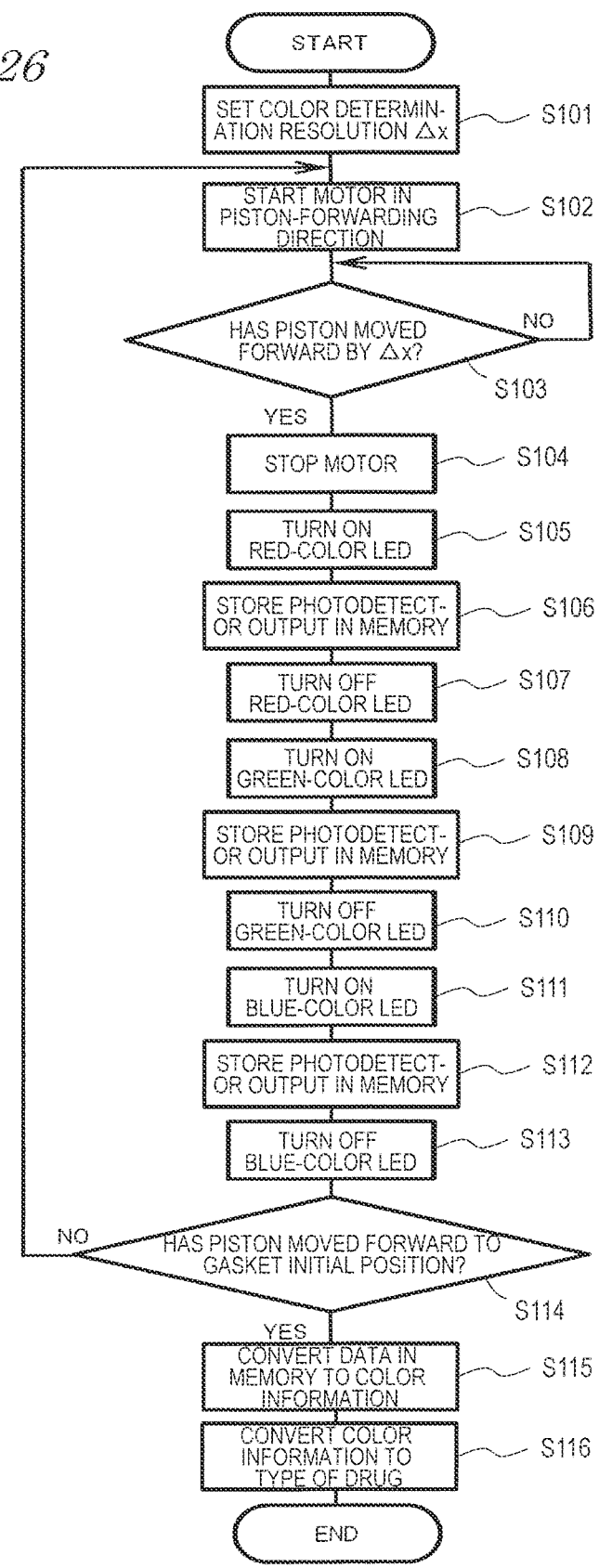
FIG. 26 is a flow chart showing an operation of the drug injection system.

[Color Determination Flow: FIG. 26]

When the color determination flow is performed, first, the resolution $\Delta x$ of the operation for detection is set (S101). The motor 22 is rotated, thereby rotating the drive gear 35 and the piston gear 105, so as to move the piston 109 forward (S102). It is determined that the amount of movement of the piston has been $\Delta x$ (S103), and if the piston 109 has moved by $\Delta x$, the motor 22 is stopped (S104).

A red-color light beam is emitted from the light emitting element 24b (S105), and the output signal from the photodetector 24a is stored in the memory 42 (S106). Then, the light emission is stopped (S107).

A green-color light beam is emitted from the light emitting element 24b (S108), and the output signal from the photodetector 24a is stored in the memory 42 (S109). Then, the light emission is stopped (S110).

A blue-color light beam is emitted from the light emitting element 24b (S111), and the output signal from the photodetector 24a is stored in the memory 42 (S112). Then, the light emission is stopped (S113).

Whether the piston 109 has reached position P3 is determined based on the number of revolutions of the motor, which is determined based on the signal from the starting point detector 24d and the signal from the rotary encoder 25 (S124), and if the piston 109 has not reached position P3, the process returns to step S102.

When the piston 109 has reached position P3, the data of the memory 42 is converted to colored information (S115), and the type of the drug is determined based on the correspondence between the color information and the second identification information of the drug cartridge 200 (S126).

Thus, the color determination flow ends.

(Alternative Designs of Drug Injection Device 11 with Cartridge Adapter 101 Loaded Therein)

Figure 27:
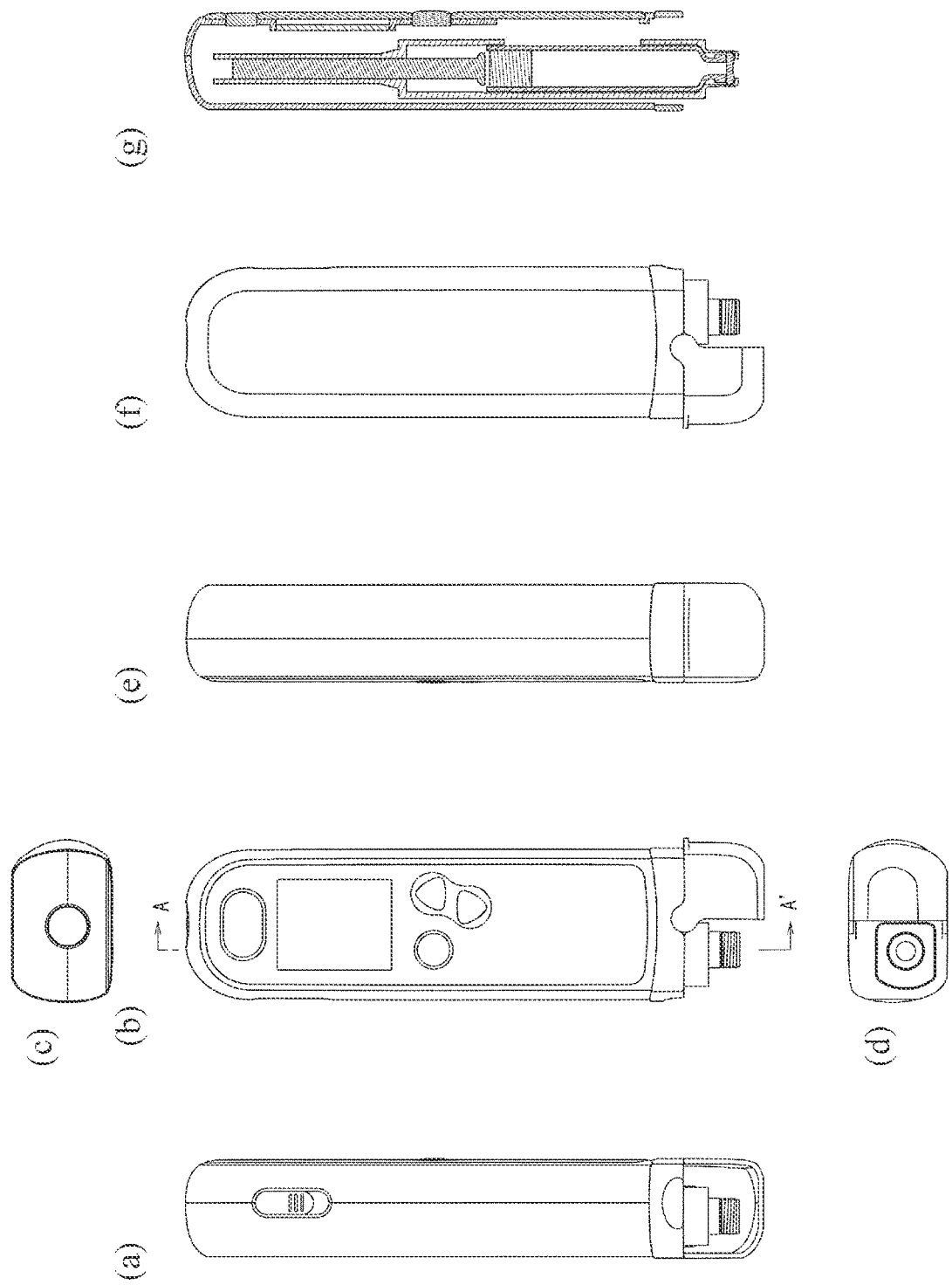
FIGS. 27(a) to 27(f) are a left side view, a front view, a plan view, a bottom view, a right side view and a back view, respectively, showing another external appearance of the drug injection device 11.
FIG. 27(g) is a cross-sectional view taken along line A-A' of FIG. 27(b).
Figure 28:
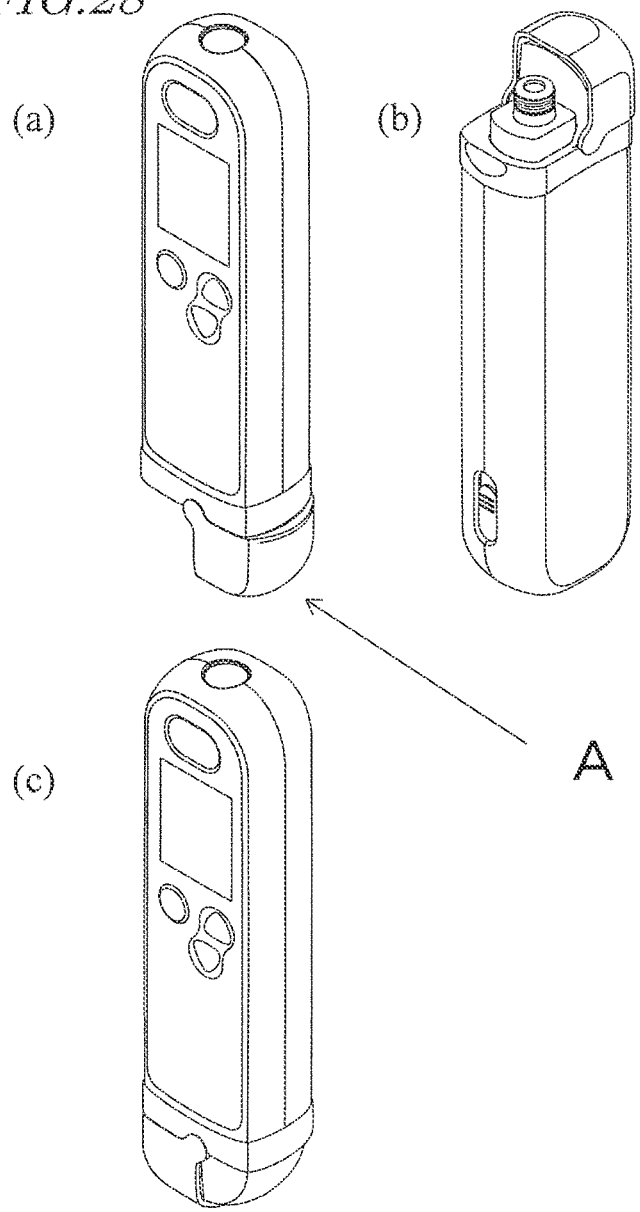
FIGS. 28(a) to 28(c) show a perspective view, a bottom perspective view and a perspective view (lid-closed state), respectively, of the drug injection device 11 shown in FIG. 27.
Figure 30:
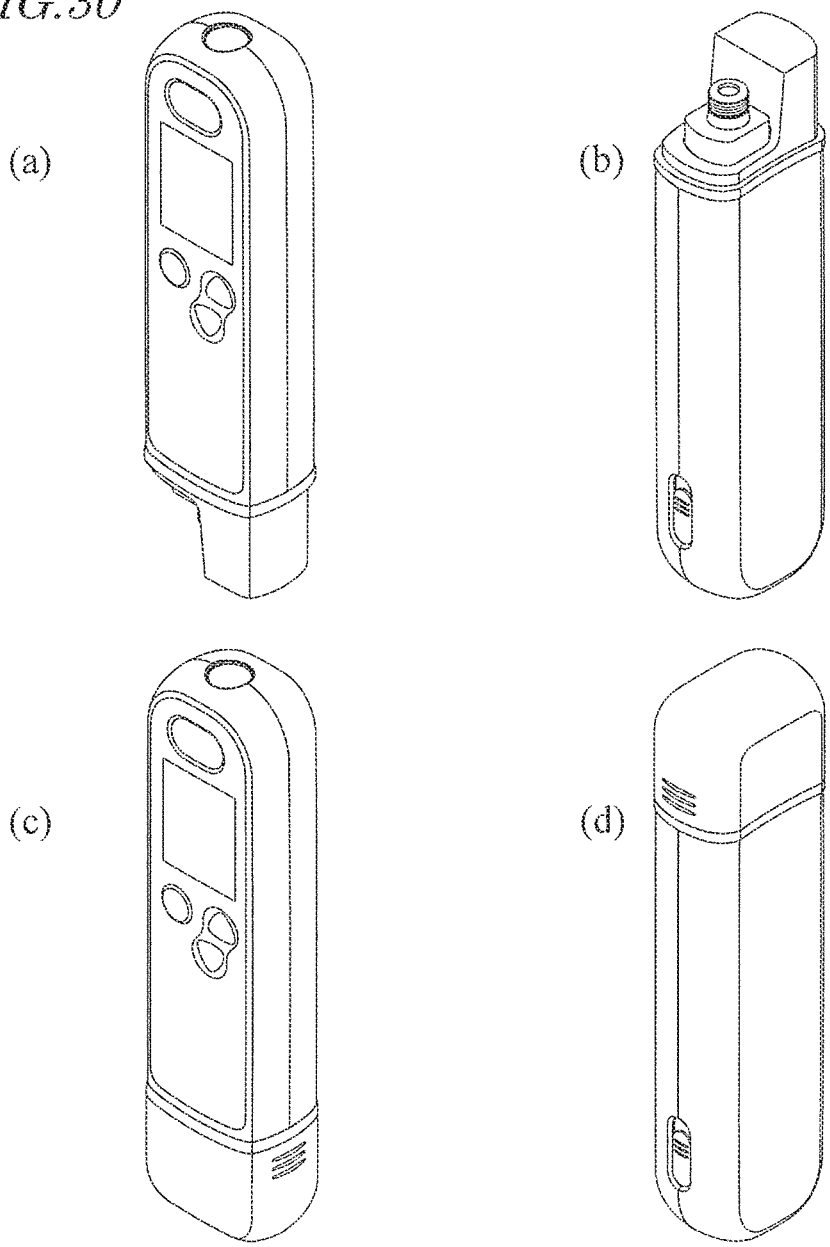
FIGS. 30(a) to 30(d) are perspective views showing another external appearance of the drug injection device 11, including reference diagram 1 showing a different distal end shape, reference diagram 2 showing the different distal end shape, reference diagram 1 showing the different distal end shape in a lid-closed state, and reference diagram 2 showing the different distal end shape in a lid-closed state.

The external appearance of the drug injection device 11 is not limited to the embodiment described above, and the drug injection device 11 may have other external appearances. For example, configurations shown in FIG. 27 to FIG. 29 or FIG. 30 may be used. With the configurations shown in FIG. 27 to FIG. 29, a pivoting cap is provided so as to protect the needle attachment portion 102 with the cartridge adapter 101 loaded in the drug injection device 11. With the pivoting cap open as shown in FIG. 28(*a*), the portion indicated by arrow A can be placed against the skin so that the drug injection device can be stably held during an injection. With the configuration shown in FIG. 30, a removable cap is provided.

(Alternative Configurations)

The embodiment described above is directed to an example in which two different drugs are administered while switching between cartridge adapters including the respective drugs therein. With the drug injection device, the cartridge adapter and the drug injection system of the present disclosure, however, three or more different drugs may be administered by switching between three cartridge adapters corresponding to the drugs.

In the embodiment described above, since the second identification information 205 is a colored region provided with a color that is unique to the drug, the second identification information detector 24 includes an element for detecting colors. When the second identification information 205 is a one-dimensional or two-dimensional barcode or an IC tag such as an RFID that corresponds to a numerical value unique to a drug, the second identification information detector 24 may be provided with a structure that is capable of detecting such information. When the second identification information 205 is a one-dimensional barcode, the second identification information can be detected by using a configuration similar to the embodiment described above or the light emitting element 24*b* that only emits light of one color. When the second identification information 205 is a one-dimensional barcode, the second identification information can be detected by performing a scanning operation similar to the embodiment described above using a line sensor as the photodetector 24*a*. Alternatively, the second identification information detector 24 may be a one-dimensional or two-dimensional barcode. When the second identification information 205 is an IC tag, the drug injection device may include an IC tag reader as the second identification information detector 24. In this case, there is no need to scan the IC tag for detecting the second identification information. Depending on the type and the capacity of the IC tag, the IC tag reader may be arranged away from the position of the second identification information of the cartridge adapter loaded in the drug injection device, and the opening 103*g* of the cartridge holder may be absent.

The lock mechanism, the anti-slip mechanism and the structure for locking the lid of the cartridge adapter described in the embodiment above are illustrative, and various modifications can be made thereto. Particularly, the positions where the depressed portion and the protruding portion are provided may be reversed from the example of the embodiment above. The force member may be any of various springs such as a coil spring, a tension spring, a leaf spring and a torsion spring. Other than metal springs, various springs made of resin may be used.

The drive gear and the piston driving mechanism are also not limited to the structures described in the embodiment above, and may be realized by other mechanical elements.

That is, the lock mechanism, the anti-slip mechanism, the structure for locking the lid of the cartridge adapter and the piston driving mechanism, may be any of various structures or mechanisms having the functions described in the embodiment above, and they may be a lock means, an anti-slip means, a means for locking the lid of the cartridge adapter and a piston driving means that are inclusive of these components.

INDUSTRIAL APPLICABILITY

The drug injection device, the cartridge adapter and the drug injection system of the present disclosure are suitably used for administering various drugs.

REFERENCE SIGNS LIST

11 Drug injection device
11*a* Opening
12 Casing
12*a* Opening
12*b* Adapter space
13 Power button
14 Injection button
15 Display section
16 Operation buttons
17 Check window
18 Lock release lever
20 Flap
21 Battery
22 Motor
23 Transmission
24 Second identification information detector
24*a* Photodetector
24*b* Light emitting element
24*c* Base
24*d* Starting point detector
24*e* Projection
25 Rotary encoder
26 Anti-slip member
27 Biasing member
28 First identification information detector
28*a* Button
29 Loading detector
29*a* Minute button
30 Engagement member
31 Control substrate
32 Drive section
33 Biasing member
34 Biasing member
35 Drive gear
35*a* Taper
36 Contact portion
41 Arithmetic circuit
42 Memory
44 Motor driver
46 Calendar clock
100 Drug injection system
101 Cartridge adapter
101' Cartridge adapter
102 Needle attachment portion
102*e* Pivot axis
103 Cartridge holder
103*a* Main body 103b Lid
103c Opening
103d Depressed portion
103f Space
103g Opening
104 Piston guide portion
104a Hole
104g First identification information
104h Loading information
104q, 104r Depressed portion
105 Piston gear
105e Female thread
105f Gear
105fa Taper
106 Gear retainer
107 Spring
108 Slide member
108a Shade portion
108b Slit
108d Protruding portion
109 Piston
109a Tip
109e Male thread
109f Flat portion
110 Piston driving mechanism
200 Drug cartridge
200' Drug cartridge
200a Distal end
201 Cylinder
201a Distal end
202 Gasket
203 Cap
204 Packing
204d Starting point detector
205 Second identification information
210 Injection needle
211 Needle
211a Rear needle
212 Cap
220a Visual feature
220b Visual feature

The invention claimed is:

1. A drug injection system comprising a cartridge adapter and a drug injection device, wherein;
the cartridge adapter comprises:
a cartridge holder having a space that can accommodate therein a drug cartridge, the drug cartridge including a cylinder having a tubular internal space extending in a longitudinal direction, a gasket supported in the internal space so as to be movable in the longitudinal direction, and a drug held in the internal space;
a piston that moves the gasket in the longitudinal direction in the internal space of the cylinder;
a piston guide that movably supports the piston and connected to the cartridge holder; and
a piston driving mechanism that drives the piston in the longitudinal direction, and
the drug injection device comprises:
a casing having an adapter space in which the cartridge adapter can be loaded, and an opening that communicates with the adapter space;
a driver that is in engagement with the piston driving mechanism of the cartridge adapter loaded in the adapter space and transmit a driving force;
an arithmetic circuit that controls the driver; and
a memory,
the piston driving mechanism of the cartridge adapter includes:
a male thread located on an outer circumference of the piston; and
a piston gear having an inner surface on which a female thread that meshes with the male thread is located and an outer surface on which gear teeth are disposed,
the driver includes a motor and a drive gear that rotates by receiving a driving force from the motor; and
in a state in which the cartridge adapter is loaded in the adapter space, the drive gear of the driver meshes with the piston gear of the piston driving mechanism.

2. The drug injection system of claim 1, wherein the drug injection device further comprises:
a flap that is movable so as to open and close the opening of the casing, wherein:
when the cartridge adapter is loaded, the flap opens the opening; and
when the cartridge adapter is pulled out, the flap shuts the opening.

3. The drug injection system of claim 1, wherein the drug injection device further comprises:
a loading detector and a first identification information detector, wherein:
the cartridge adapter further includes first identification information in accordance with a type of the drug cartridge to be accommodated therein;
the loading detector detects loading of the cartridge adapter; and
the first identification information detector detects the first identification information of the drug cartridge.

4. The drug injection system of claim 3, wherein:
the memory stores information of an injection schedule; and
based on the information of the injection schedule and the detection results of the loading detector and the first identification information detector, the arithmetic circuit causes the display to produce a display that is corresponding to the visual feature in accordance with a type of a drug that should be loaded, if no cartridge adapter is loaded or if a cartridge adapter of a drug that is not according to the injection schedule is loaded.

5. The drug injection system of claim 1, wherein the drug injection device further comprises:
a display, wherein:
based on a detection result of the first identification information detector, the arithmetic circuit causes the display to display a feature that is corresponding to the visual features of the drug cartridge and the cartridge adapter.

6. The drug injection system of claim 1, wherein the drug injection device further comprises a lock mechanism, the lock mechanism including an engagement member that is in engagement with the cartridge adapter placed in the adapter space, and a release lever that releases the engagement between the engagement member and the cartridge adapter.

7. The drug injection system of claim 6, wherein the drug injection device further comprises an anti-slip mechanism that is in engagement with the cartridge adapter so as to prevent the cartridge adapter from slipping off the adapter space in a state in which the lock mechanism is released.

8. The drug injection system of claim 1, wherein the drag injection device further comprises:
a second identification information detector, wherein:
the drug cartridge has unique second identification information in accordance with the drug; and the second identification information detector detects the second identification information of the drug cartridge.

9. The drug injection system of claim 8, wherein:
the second identification information is a colored region provided with a color that is unique to the drug; and
the second identification information detector detects the color of the colored region of the drug cartridge.

10. The drug injection system of claim 9, wherein:
the second identification information detector includes a base, and a photodetector and a light emitting element located on the base;
the cartridge holder has an opening that exposes therethrough at least a portion of the colored region of the drug cartridge;
in a state in which the drug cartridge that is unused is accommodated in the cartridge holder, the piston is movable between a first, most retracted position at which there is a predetermined interval between a distal end of the piston and the gasket, and a second position at which the distal end of the piston and the gasket are in contact with each other and at which the gasket is inserted farthest into the cylinder;
the cartridge adapter further includes a slide member that moves in the longitudinal direction as the piston moves from the first position to a third position at which the piston is in contact with the gasket;
the slide member has a shade portion that covers a portion of the opening of the cartridge holder and a slit that is located in the shade portion;
as the slide member moves, the slit scans the colored region of the drug cartridge in the longitudinal direction; and
as the base of the second identification information detector moves in the longitudinal direction together with the slide member of the cartridge adapter, the second identification information detector detects the color based on light that enters through the slit of the slide member.

11. The drug injection system of claim 1, wherein, in the cartridge adapter, a taper is provided on an end surface of each of the gear teeth.

12. The drug injection system of claim 11, wherein in the cartridge adapter, the gear teeth are partially exposed from the opening of the cartridge holder to receive a drive force from drug injection device.

* * * * *